United States Patent
DaRosa

(10) Patent No.: US 10,617,565 B2
(45) Date of Patent: Apr. 14, 2020

(54) SAFETY SYSTEM, APPARATUS AND METHOD

(71) Applicant: Safe Tool Technology Corporation, So. Easton, MA (US)

(72) Inventor: Curt DaRosa, Berkley, MA (US)

(73) Assignee: Safe Tool Technology Corporation, So. Easton, MA (US)

( * ) Notice: Subject to any disclaimer, the term of this patent is extended or adjusted under 35 U.S.C. 154(b) by 0 days.

(21) Appl. No.: 15/965,104

(22) Filed: Apr. 27, 2018

(65) Prior Publication Data

US 2019/0000675 A1     Jan. 3, 2019

Related U.S. Application Data

(63) Continuation-in-part of application No. 15/856,849, filed on Dec. 28, 2017, now Pat. No. 10,022,272, (Continued)

(51) Int. Cl.
*F16P 3/00*     (2006.01)
*A61F 9/02*     (2006.01)
(Continued)

(52) U.S. Cl.
CPC ............... *A61F 9/02* (2013.01); *A61F 9/029* (2013.01); *F16P 3/00* (2013.01); *F16P 3/147* (2013.01);
(Continued)

(58) Field of Classification Search
CPC .. H01R 13/6392; H01R 13/62; H01R 13/627; H01R 13/639; H01R 43/027; B25F 5/00;
(Continued)

(56) References Cited

U.S. PATENT DOCUMENTS

| | | |
|---|---|---|
| 2,753,536 A | 7/1956 | Tjader |
| 4,515,521 A | 5/1985 | Takeo et al. |

(Continued)

FOREIGN PATENT DOCUMENTS

DE     19741931 A1     6/2000

OTHER PUBLICATIONS

International Search Report and Written Opinion from corresponding International Application No. PCT/US18/040303 (dated Sep. 20, 2018).

*Primary Examiner* — Benyam Haile
(74) *Attorney, Agent, or Firm* — Rhodes Donahoe, LLC; Robert V. Donahoe

(57) ABSTRACT

An apparatus for use with an item of personal protective equipment, where the item of personal protective equipment includes a sensor configured to detect when the personal protective equipment is being worn properly by the user. The apparatus is housed within a hand-held power tool that includes a power circuit. The apparatus includes an electrical isolation device configured to prevent current flow in at least one conductor included in the power circuit; a wireless communication device configured to wirelessly couple to a wireless communication device included in the personal protective equipment. The wireless communication device is configured to receive a wireless signal transmitted from the wireless communication device included the personal protective equipment, the wireless signal providing information concerning whether the user is wearing the item of personal protective equipment properly. The electrical isolation device operates to allow current flow in the at least one conductor when the information provided by the wireless signal indicates that the item of personal protective equipment is being worn properly by the user.

15 Claims, 16 Drawing Sheets

Related U.S. Application Data which is a continuation of application No. 15/639,238, filed on Jun. 30, 2017, now Pat. No. 9,895,265.

(51) Int. Cl.

| | | |
|---|---|---|
| *G02C 1/00* | (2006.01) | |
| *G02C 9/00* | (2006.01) | |
| *F16P 3/14* | (2006.01) | |
| *G08B 21/02* | (2006.01) | |
| *G02C 11/00* | (2006.01) | |
| *A61F 9/00* | (2006.01) | |
| *G08B 21/00* | (2006.01) | |
| *H04W 4/80* | (2018.01) | |
| *H01R 13/639* | (2006.01) | |
| *H01R 13/62* | (2006.01) | |
| *B25F 5/00* | (2006.01) | |

(52) U.S. Cl.
CPC ............... *F16P 3/148* (2013.01); *G02C 1/00* (2013.01); *G02C 9/00* (2013.01); *G02C 11/10* (2013.01); *G08B 21/02* (2013.01); *A61F 9/00* (2013.01); *B25F 5/00* (2013.01); *F16P 3/008* (2013.01); *G08B 21/00* (2013.01); *H01R 13/62* (2013.01); *H01R 13/6392* (2013.01); *H04W 4/80* (2018.02)

(58) Field of Classification Search
CPC .... F16P 3/00; F16P 3/008; F16P 3/147; F16P 3/148; G08B 21/00; G08B 21/02; H04W 4/008

See application file for complete search history.

(56) References Cited

U.S. PATENT DOCUMENTS

| | | |
|---|---|---|
| 5,315,289 A | 5/1994 | Fuller et al. |
| 5,666,010 A | 9/1997 | Stratiotis |
| 5,796,341 A | 8/1998 | Stratiotis |
| 5,903,423 A | 5/1999 | Okano et al. |
| 7,982,624 B2 | 7/2011 | Richter et al. |
| 8,514,085 B2 | 8/2013 | Nelson et al. |
| 9,126,334 B2 | 9/2015 | Nakamura et al. |
| 9,237,633 B2 | 1/2016 | Oh |
| 9,367,976 B2 | 6/2016 | Logan et al. |
| 9,895,265 B1 | 2/2018 | DaRosa |
| 2009/0273436 A1* | 11/2009 | Gluck ............... H04L 63/10 340/5.2 |
| 2011/0309936 A1* | 12/2011 | Nelson ............... F16P 3/142 340/573.1 |
| 2012/0326837 A1 | 12/2012 | Ajay et al. |
| 2013/0079850 A1 | 3/2013 | Darvish |
| 2014/0163402 A1* | 6/2014 | Lamego ............. A61B 5/02141 600/493 |
| 2014/0312033 A1 | 10/2014 | Van Der Linde et al. |
| 2015/0162646 A1* | 6/2015 | Kawase ............. H01M 2/1022 429/7 |
| 2015/0378323 A1 | 12/2015 | Nelson et al. |
| 2017/0136875 A1 | 5/2017 | Logan et al. |

* cited by examiner

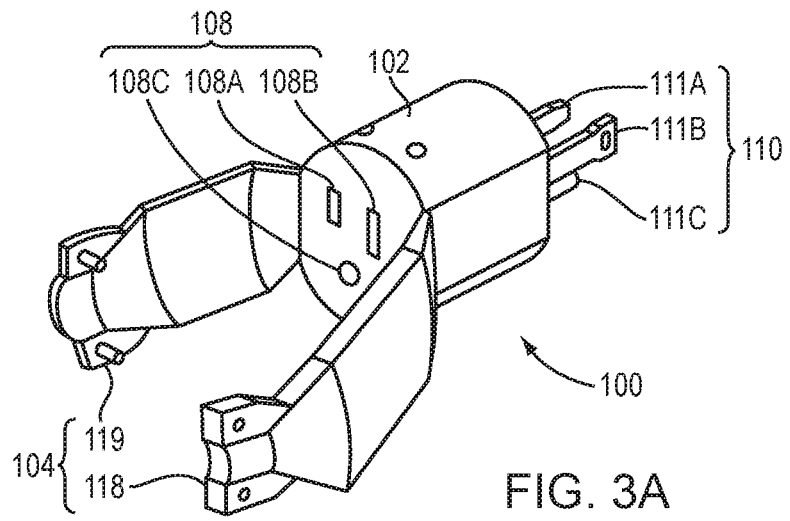
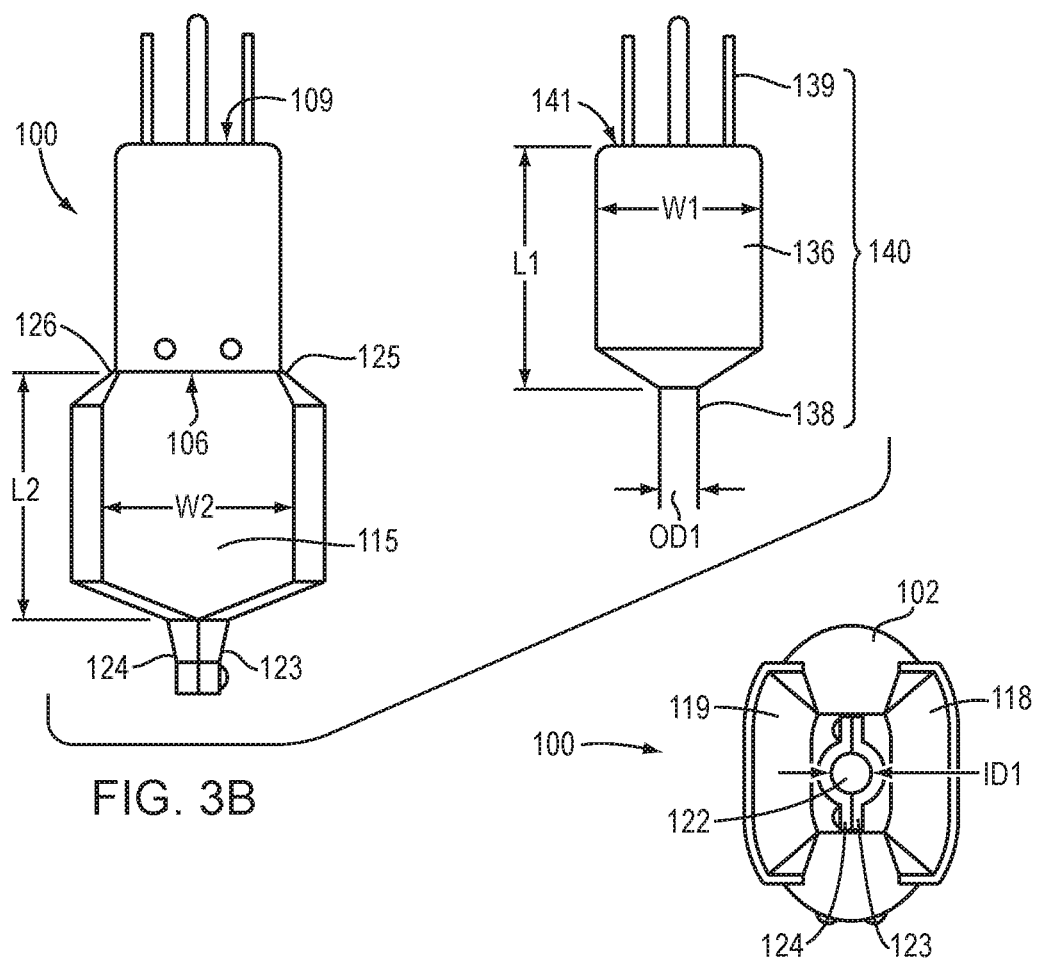
FIG. 3A
FIG. 3B
FIG. 3C

SAFETY SYSTEM, APPARATUS AND METHOD

RELATED APPLICATIONS

This application is a continuation-in-part of, and claims priority under 35 U.S.C. § 120 to co-pending U.S. patent application Ser. No. 15/856,849 entitled "SYSTEM, APPARATUS AND METHOD FOR EYE PROTECTION," filed on Dec. 28, 2017, which is a continuation of, and claims priority under 35 U.S.C. § 120 to U.S. Pat. No. 9,895,265 entitled "SAFETY APPARATUS AND SYSTEM FOR USE WITH EYE PROTECTION," filed on Jun. 30, 2017, the disclosure of each of the preceding is herein incorporated by reference in its entirety.

BACKGROUND OF INVENTION

1. Field of Invention

This invention relates generally to apparatus, systems and methods for increasing the safety of personnel operating tools and equipment. More specifically, at least one embodiment, relates to systems, apparatus and methods providing improved safety for operators of electrically powered tools and equipment.

2. Discussion of Related Art

More than 800,000 individuals sustain an eye injury annually in U.S. workplaces. Tens or hundreds of thousands of other individuals sustain an eye injury outside of the workplace annually. Workplace eye injuries alone cost an estimated 300 million dollars in lost productivity, medical treatment and worker's compensation. Frequently, these injuries result from the use of power equipment without eye protection, for example, operation of electrically operated hand tools.

Traditional approaches to eye-safety have developed over time in an effort to reduce eye injuries. For example, systems have been developed to prevent the operation of certain types of medical equipment unless operating personnel are wearing prescribed safety equipment. These and other approaches also employed in industrial settings generally focus on a fixed piece of equipment. Some of these prior approaches are location-based and rely on the fact that the equipment that requires the use of safety equipment will not be moved from the location.

Another approach employs a key lock to lock a switch to the prongs on a plug located at the end of a power cord for a specific piece of equipment. However, application of the preceding is very limited because of the nature of the connection between the lock and a specific type of plug. In addition, an integrated key lock creates a complex mechanical device. Other approaches are directed to an automatic shutoff based on a lack of motion of a piece of equipment. However, these approaches require a physical connection to a sensor included in the piece of electrically operated equipment or employ a device that is included as an integral part of the power cord of the piece of equipment.

SUMMARY OF INVENTION

Therefore, there is a need for apparatus and systems that provide an adaptable safety system that is better suited to the dynamics found in most workplaces. These approaches provide apparatus and systems that provide a safety interlock that is not restricted to a specific location or a specific piece of equipment. Some of these embodiments provide an approach that is much more universal than conventional approaches because the apparatus is designed to secure to the power cords most commonly employed with electrical equipment in the workplace and/or by home hobbyists. According to some further embodiments, a safety apparatus is configured to a secure to the distal end of an extension cord that can be employed with any number of electrically operated pieces of equipment. Further, approaches described herein can allow users to easily attach and secure the safety apparatus to a power cord using common hand tools. Where a lockable apparatus is desired, embodiments described herein allow for the use of conventional padlocks rather than the equipment-specific and specially designed hardware required of prior approaches.

According to one aspect, an apparatus assists a user in employing safety glasses. In various embodiments, the apparatus includes a body housing an electrical isolation device and a wireless communication device. According to one embodiment, the body includes a first end defining a female electrical socket and a second end defining a male electrical plug. According to a further embodiment, a set of jaws is coupled to the body and includes an end proximate the body and a distal end configured to secure to an electrical cord that is electrically coupled to the body at one of the first end or the second end. The electrical isolation device is located in series between a conductor included in the female electrical socket and a corresponding conductor included in the male electrical plug. The wireless communication device is configured to receive a wireless signal transmitted from the safety glasses, the wireless signal providing information concerning whether the user is wearing the safety glasses. The electrical isolation device is configured to prevent current flow between the conductor included in the female electrical socket and the corresponding conductor included in the male electrical plug when the safety glasses are not being worn by the user. The electrical isolation device is configured to complete an electrical circuit to allow current flow between the conductor included in the female electrical socket and the corresponding conductor included in the male electrical plug when the safety glasses are being worn by the user.

According to another aspect, a safety kit is configured for retail sale. According to various embodiments, the safety kit includes: a package configured for display at a retail point-of-sale location; safety glasses disposed in the package, the safety glasses including an electronic system including a sensor configured to detect when the safety glasses are worn by a user and a Bluetooth communication device; and an apparatus disposed in the package. According to one embodiment, the apparatus includes a body housing an electrical isolation device and a Bluetooth communication device. According to a further embodiment, the body includes a first end defining a female electrical socket configured to receive a three prong plug including a line conductor, a neutral conductor and a ground conductor; and a second end defining a male electrical plug configured with a line conductor, a neutral conductor and a ground conductor. The apparatus further includes a set of jaws coupled to the body and configured to secure to an electrical cord that is electrically coupled to the body at one of the first end or the second end. The electrical isolation device is located in series between a line conductor included in the female electrical socket and the line conductor included in the male electrical plug. The Bluetooth communication device included in the body is configured to receive a wireless signal transmitted from the Bluetooth communication device included in the safety glasses, the wireless signal providing information concerning whether the user is wearing the safety glasses. The electrical isolation device is configured to prevent current flow in the line conductor included in the body when the safety glasses are not being worn by the user. The electrical isolation device is configured to complete an electrical circuit to allow current flow in the line conductor included in the body when the safety glasses are being worn by the user.

According to still another aspect, a safety system includes: safety glasses including an electronic system having a sensor configured to detect when the safety glasses are worn by a user and a wireless communication device; and an apparatus. According to one embodiment, the apparatus includes: a body housing an electrical isolation device and a wireless communication device; and a fastening device coupled to the body. According to a further embodiment, the body includes: a first end defining a female electrical socket coupled to a line conductor included in the body, a neutral conductor included in the body and a ground conductor included in the body, the female electrical socket configured to couple to a three prong plug including a line conductor, a neutral conductor and a ground conductor; and a second end defining a male electrical plug coupled to the line conductor included in the body, the neutral conductor included in the body and the ground conductor included in the body. According to a still further embodiment, the fastening device is configured to move from an open position to a closed position in which an electrical cord that is electrically coupled to the body at one of the first end or the second end is also physically secured to the body by the fastening device. The electrical isolation device is located in series in the line conductor included the body between the female electrical socket and the male electrical plug. The wireless communication device included in the body is configured to receive a wireless signal transmitted from the wireless communication device included in the safety glasses, the wireless signal providing information concerning whether the user is wearing the safety glasses. The electrical isolation device is configured to prevent current flow in the line conductor included in the body when the safety glasses are not being worn by the user. The electrical isolation device is configured to complete an electrical circuit to allow current flow in the line conductor included in the body when the safety glasses are being worn by the user.

According to yet another aspect, an apparatus is provided for use with an item of personal protective equipment. The item of personal protective equipment includes a first wireless communication device and a sensor configured to detect when the personal protective equipment is being worn properly by the user. The apparatus is configured to be housed within a hand-held power tool that includes a power circuit to supply electrical power for operation of the hand-held power tool. According to some embodiments, the apparatus includes an electrical isolation device configured to prevent current flow in at least one conductor included in the power circuit, a second wireless communication device configured to wirelessly couple to the first wireless communication device. The second wireless communication device is configured to receive a wireless signal transmitted from the first wireless communication device, the wireless signal providing information concerning whether the user is wearing the item of personal protective equipment properly. The electrical isolation device operates to allow current flow in the at least one conductor when the information provided by the wireless signal indicates that the item of personal protective equipment is being worn properly by the user.

According to a still further aspect, a safety system is provided for a user employing each of eye protection hardware including a first wireless communication device and a first power cord including a male plug and a second power cord including a female socket. According to various embodiments, the system includes a first component configured to secure to a respective one of the first power cord and the second power cord and a second component. According to one embodiment, the second component includes a longitudinal axis, at least one line conductor, an electrical isolation device configured to prevent current flow in the at least one line conductor, a second wireless communication device configured to wirelessly couple to the first wireless communication device, a body housing the electrical isolation device and the second wireless communication device and a fastening device coupled to the body. According to a further embodiment, the body includes a first end defining a female electrical socket coupled to the at least one line conductor included in the body, the female electrical socket configured to electrically couple to the first power cord, a second end defining a male electrical plug coupled to the at least one line conductor, the male electrical plug included in the body configured to electrically couple to the second power cord; and a distal end selected from one of the first end and the second end. In one embodiment, the fastening device includes a distal end. In various embodiments, the fastening device configured to move in a direction parallel to the longitudinal axis from a first position to a second position in which the distal end of the fastening device extends beyond the distal end of the body to receive the respective one of the first power cord and the second power cord and properly align the fastening device to secure the first component to the second component. According to these embodiments, the second wireless communication device is configured to receive a wireless signal transmitted from the first wireless communication device, the wireless signal providing information concerning whether the user is wearing the safety glasses. The electrical isolation device is configured to allow current flow in the at least one line conductor when the information provided by the wireless signal indicates that the safety glasses are being worn by the user.

In still another aspect, an apparatus is configured for use with a first power cord, a second power cord and safety glasses including a first wireless communication device. In various embodiments, the apparatus includes at least one line conductor, an electrical isolation device configured to prevent current flow in the at least one line conductor, a second wireless communication device configured to wirelessly couple to the first wireless communication device, a body housing the electrical isolation device and the second wireless communication device and a collar. According to one embodiment, the body includes a longitudinal axis, a first end defining a female electrical socket coupled to the at least one line conductor, the female electrical socket configured to electrically couple to the first power cord, a second end defining a male electrical plug coupled to the at least one line conductor, the male electrical plug configured to electrically couple to the second power cord and a distal end selected from one of the first end and the second end. According to some embodiments, the collar is configured to move in a direction parallel to the longitudinal axis while coupled to the body. The collar includes an interior wall that defines a hollow region sized and configured to receive at least a portion of the body therein. Further, the collar configured to secure to one of the female electrical socket and the male electrical plug with the respective one of first power cord and the second power cord electrically coupled to the distal end of the body and the collar at least partially extended from the body in a direction of the distal end. According to these embodiments, the second wireless communication device is configured to receive a wireless signal transmitted from the first wireless communication device, the wireless signal providing information concerning whether the user is wearing the safety glasses. The electrical isolation device is configured to allow current flow in the at least one line conductor when the information provided by the wireless signal indicates that the safety glasses are being worn by the user.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings:

FIGS. 3A-3C illustrate different views of the safety device of FIG. 1;

DETAILED DESCRIPTION

Figure 1:
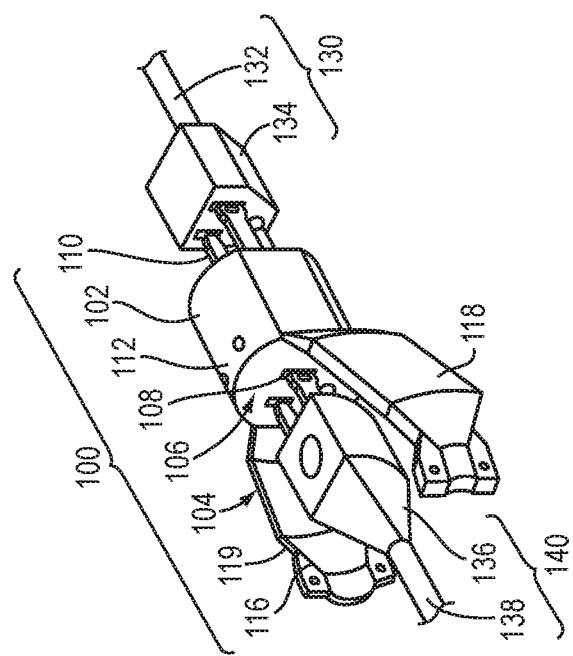
FIG. 1 illustrates a safety device in accordance with one embodiment.
Figure 1:
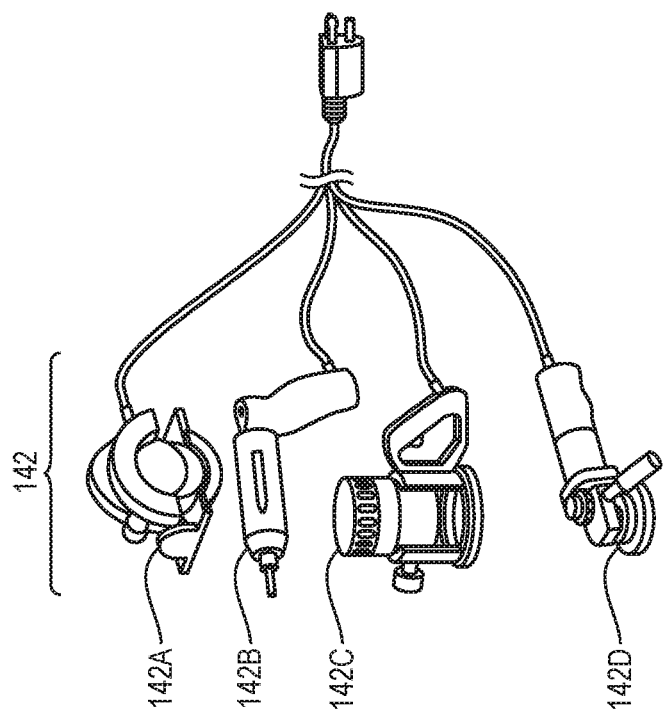

This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing", "involving", and variations thereof herein, is meant to encompass the items listed thereafter and equivalents thereof as well as additional items.

Referring now to FIG. 1, a safety device 100 is illustrated in accordance with one embodiment. The safety device 100 includes a body 102, a fastening device 104, a first face 106, a female socket 108 located in the first face, a male plug 110 and a user interface 112. FIG. 1 also illustrates an extension cord 130 including a cord 132 and a female socket 134 located at the distal end of the extension cord 130. In addition, FIG. 1 illustrates a power cord 140 including a male plug 136 and a cord 138. The power cord 140 can be included in an electrically operated hand tool 142, for example, a circular saw 142A, a drill 142B, a router 142C and a grinder 142D. One of ordinary skill in the art in view of the disclosure provided herein will recognize the preceding list is non-exhaustive. Thus, while the illustrated embodiment shows a mix of conventional power tools, other hand tools can be employed with the safety device 100, for example, electrically-operated lawn mowers, hedge trimmers, weed whackers and vacuums to name a few. Further, the electrically-operated equipment can be fixed in place, for example, bench-mounted tools or equipment such as a drill press.

As is described in greater detail below, the safety device 100 includes an electronic system in the body 102 that allows the device 100 to communicate with a pair of safety glasses. In general, the electronic system includes an electrical isolation device to maintain an open circuit in one or more line conductors included in the body 102 to prevent operation of equipment (for example, the power tool 142) plugged into the device 102 unless the electronic systems receives information communicated from the safety glasses that indicates the safety glasses are being worn properly.

In various embodiments, the conductors located in the body 102 connect the conductors included in the female socket 108 with the corresponding conductors included in the male plug 110. For example, in a single phase device, the line conductor included in the male plug 110 is connected to the line conductor in the female socket 108, the neutral conductor included in the male plug 110 is connected to the neutral conductor in the female socket 108 and the ground conductor included in the male plug 110 is connected to the ground conductor included in the female receptacle 108.

In various embodiments, the body 102 is manufactured from a material having electrical insulating properties sufficient to maintain electrical isolation between the conductors located in the body 102. Further, the materials of construction of the body 102 safely insulate the conductors from a user who takes hold of the body 102. In further embodiments, the required electrical insulation rating is determined based on the voltage rating of the device, for example, 120 VAC, 240 VAC, etc.

The fastening device 104 allows the safety device 100 to receive the cord 140 of the power tool 142 and securely attach the cord 140 to the device 100 with the cord 140 plugged into the female socket 108 located in the face 106. The male plug 110 is an integral part of the safety device 100 and is configured to plug into the distal end of the extension cord 130. According to the illustrated embodiment, the fastening device 104 includes a fastener 116, a first wall 118 and a second wall 119. In the illustrated embodiment, the first wall 118 and the second wall 119, respectively, are hingedly attached to the body 102 such that they are moved apart to place the fastening device 104 in an open position. To place the fastening device 104 in the closed position, the first wall 118 and the second wall 119 are moved together to place the respective distal ends of walls 118, 119 adjacent to one another. According to the illustrated embodiment, the respective distal ends of walls 118, 119 are secured to one another by the fastener 116. According to the illustrated embodiment, the fastener 116 includes two screws. As is described in greater detail below, other fastening structure can be used alone or in combination with a mechanical fastener.

The user interface 112 can vary depending on the embodiment. According to the illustrated embodiment, the user interface 112 provides two indicating lamps, for example, a red indicating lamp and a green indicating lamp (e.g., LEDs). In one embodiment, the red indicating lamp provides a status indication concerning the state of the electrical isolation device and the green indicating lamp provides an indication of whether the safety device 100 is connected to an active source of electricity. According to this embodiment, the green indicating lamp is on when the safety device 100 is connected to an active (i.e., "energized") electrical circuit, for example, with the extension cord 130 connected and plugged into an energized source of electricity. The red indicating lamp is on with the electrical isolation device is closed as a result of the proper use of the safety glasses associated with the device 100. In another embodiment, the red lamp can indicate that the electrical isolation device is in a first state that prevents current flow between the male plug 110 to the female socket 108. The green lamp can indicate that the electronic system has placed the electrical isolation device in a second state to permit current flow between the male plug 110 to the female socket 108. In one embodiment, the change of state is a result of feedback from the safety glasses concerning whether the safety glasses are being worn properly.

The user interface can include different elements either alone or in combination with indicating lamps depending on the embodiment. Thus, the user interface 112 can include one or more switches or pushbuttons, for example, to allow a user to turn the electronic system included in the safety device "on" or to activate a wireless communication system included in the safety device 100. The user interface 112 can also include additional or different indicating lamps. In one embodiment, the user interface 112 includes an indicating lamp that identifies when the wireless communication system included in the safety device 100 is in communication with a wireless communication system included in the safety glasses. For example, the indicating lamp can turn on when the communications systems of the safety device and the safety glasses are "paired" for communication with one another. According to still another embodiment, the user interface includes a speaker to provide an audio output that can provide feedback to the user regarding the operating status of the safety system including the safety device 100 and/or the status one or more features included in the device 100.

Figure 2:
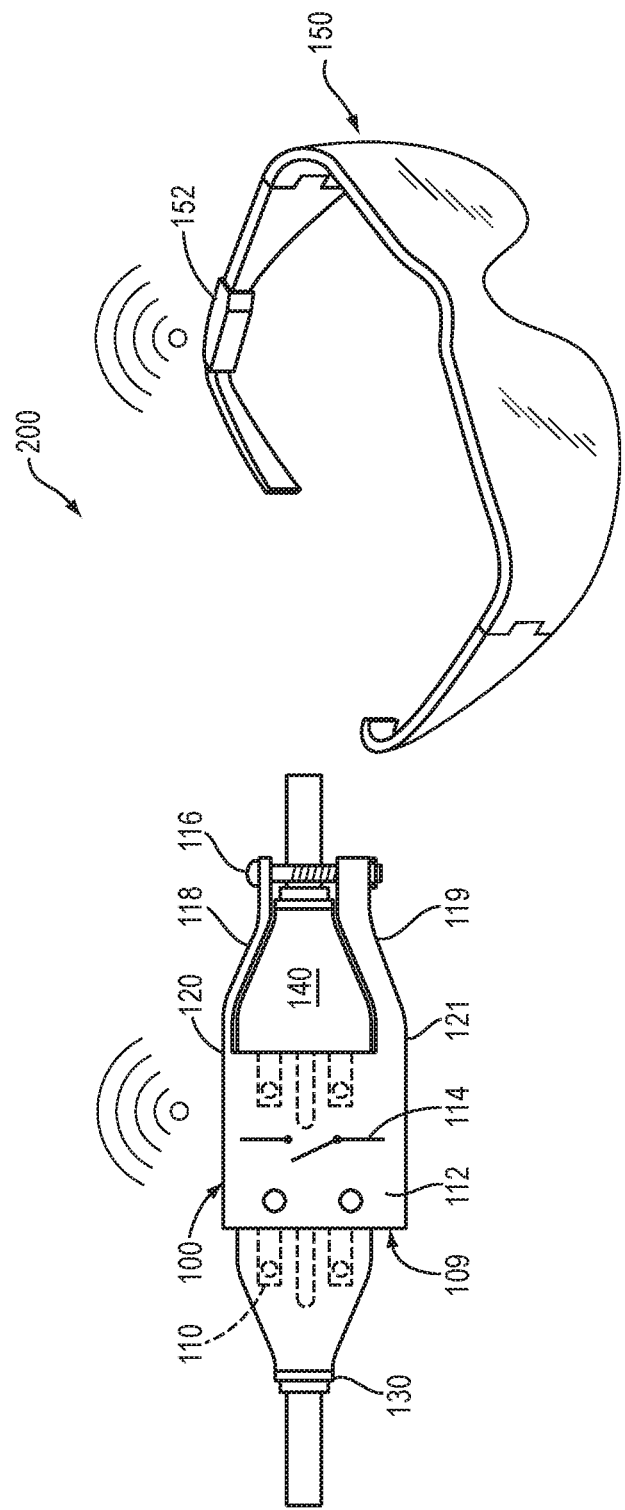
FIG. 2 illustrates a safety system including the safety device of FIG. 1 in accordance with one embodiment.

Referring now to FIG. 2, a safety system 200 including the safety device 100 with a pair of safety glasses 150 is illustrated in an embodiment in which the device 100 and glasses 150 are configured to wirelessly communicate with one another. According to the illustrated embodiment, the safety glasses 150 include an electronic apparatus 152. As is described in greater detail herein, the electronic apparatus 152 can include one or more sensors to detect whether the safety glasses are being worn properly. FIG. 2 illustrates the user interface 112 and an electrical isolation device 114. Other elements of the electronic system included the body are described below with reference to FIG. 5. FIG. 2 also illustrates a first hinge 120, a second hinge 121 and a face 109 which is included in the body. According to this embodiment, the male plug 110 extends from the face 109.

According to some embodiments, the first wall 118 and the second wall 119 are hingedly connected to the body 102 on opposite sides of the body from one another. The first wall 118 is attached to the body at the first hinge 120 while the second wall 119 is attached to the body at the second hinge 121. According to other embodiments, only a single hinge can be employed where, for example, only one wall of the fastening device pivots while a second wall remains substantially fixed in place. In this embodiment, a position of the single movable wall is adjusted to move the fastening device between the open position and the closed position. According to still another embodiment, hinges are not employed in any of the walls of the fastening device. According to this embodiment, the shape and materials of construction of the fastening device provide a natural resiliency that allows the fastening device to be moved between the open position and the closed position by deformation of the walls. This resiliency causes the distal ends of the walls of the fastening device to "spring" apart from one another when the fastener 116 releases the respective distal ends of the walls from engagement with one another. Further, while FIG. 2 illustrates a configuration in which the first wall 118 and the second wall 119 are attached to opposing sides of the body, other relative orientations of the two walls 118, 119 can be employed provided that they allow the power cord 140 to be secured to the safety device 100 by the fastening device 104.

In the embodiment illustrated in FIG. 2, the safety device 100 is connected to each of the extension cord 130 and the power cord 140. The male plug 110 is connected to the distal end of the extension cord 130 such that the face 109 meets a corresponding face of the extension cord. The power cord 140 is received in a cavity formed in the fastening device 104 when the fastening device is placed in the closed position. In particular, the male plug 136 is received in the cavity and the cord 138 extends from the cavity via an opening located at the distal end of the fastening device 104.

According to various embodiments, the electronic apparatus 152 detects a status of the safety glasses to determine whether the safety glasses are being worn properly. For example, the electronic apparatus 152 can include one or more switches, biometric sensors and/or inertial sensors used alone, in combination with one another or in combination with other devices to determine whether the safety glasses are being worn properly.

In operation, the safety system 200 ensures that a user is properly wearing the safety glasses 150 before the isolation device 114 is placed in a state in which the female socket 108 is energized such that the equipment connected by the power cord 140 can be operated. For example, where a proximate end of the extension cord 130 is plugged into an energized wall outlet and the male plug 110 is plugged into the socket located at a distal end of the extension cord 130 electricity is present at the safety device 100. If the safety glasses 150 are not being worn, the safety device 100 receives a signal from the electronic apparatus 152 indicating that the glasses 150 are not being worn. Based on that information, the safety device 100 is placed in a first state in which the isolation device 114 maintains the female socket 108 in a de-energized state, for example, by preventing current flow from the male plug 110 to the female socket 108. When the safety glasses 150 are being worn, the electronic apparatus 152 wirelessly communicates the updated status to the safety device 100. In response, the safety device 100 is placed in a second state in which the isolation device operates to allow current flow from the male plug 110 to the female socket 108 thereby energizing the female socket 108. As a result, the equipment connected to the power cord 140 can now be operated by the user.

Referring now to FIG. 3A, the safety device 100 is illustrated in accordance with various embodiments. According to this embodiment, the fastening device 104 is located to securely attach to the power cord of a piece of electrically operated equipment. As mentioned above, the electrically operated equipment can include portable equipment that is freely moved about by a user (for example, an electrically-operated hand drill) or a fixed piece of equipment (for example, a drill press). In the illustrated embodiment, the fastening device 104 includes the first side wall 118 and the second side wall 119 in an arrangement in which they are pivotably attached to the body 102 and operate like a set of jaws to move between the open position and the closed position in which the power cord is secured to the body 102.

Details concerning the female socket 108 are also illustrated in FIG. 3A. In the illustrated embodiment, the female socket 108 includes a line-conductor socket 108A, a neutral-conductor socket 108B and a ground-conductor socket 108C. Each of these sockets is connected to a corresponding prong included in the male plug 110. According to the illustrated embodiment, the male plug 110 includes a line conductor 111A, a neutral conductor 111B and a ground conductor 111C. In the preceding arrangement, the line-conductor socket 108A is connected to the line conductor 111A, the neutral-conductor socket 108B is connected to the neutral conductor 111B and the ground-conductor socket 108C is connected to the ground conductor 111C. According to a further embodiment, the isolation device (for example, the isolation device 114 illustrated in FIG. 2) is connected in series within the body between the line-conductor socket 108A and the line conductor 111A.

Referring now to FIG. 3B, a top view of the safety device 100 and the power cord 140 are illustrated with the device 100 and the power cord 140 located in positions adjacent to one another. The power cord 140 includes a face 141 located at a distal end of the plug 136. A set of conductors 139 extends from the face 141. The set of conductors 139 includes a line conductor, a neutral conductor and a ground conductor arranged in a conventional layout that allows the socket 108 to receive the conductors 139. The plug 136 includes dimensions including a width W1 and a length L1. The cord 138 includes an outside diameter OD1.

In the embodiment illustrated in FIGS. 3A-3B, the fastening device 104 includes a first distal end 123 located at a distal end of the first wall 118. The fastening device 104 also includes a second distal end 124 located at a distal end of the second wall 119. A first proximate end 125 is located at a proximate end of the first wall 118. A second proximate end 126 is located at a proximate end of the second wall 119. FIG. 3B illustrates the fastening device in the closed position in which the first wall 118 and the second wall 119 are pivoted together such that the first distal end 123 and the second distal end 124 are located adjacent to one another. According to some embodiments, the first distal end 124 and the second distal end 125 are in contact with one another with the fastening device 104 in the closed position.

Although embodiments illustrated herein show the use of a mechanical fastener (for example, the fastener 116), other fastening structure can be provided to secure the first distal end 123 to the second distal end 124 according to alternate embodiments. For example, a latch can be integrally formed as a feature of the first distal end 123 and the second distal end 124. According to this embodiment, the latch can securely fasten the respective distal ends 123, 124 to one another when the fastening device 104 is moved to the closed position. Where the fastening device 104 is formed of a plastic material, for example, injection molded, one or more elements of the latch can be molded into the first distal end 123 with corresponding features molded into the second distal end 124 to provide a snap-fit closure. In other embodiments, the fastening device 104 can include a fastening element on one of the distal ends 118, 119 that moves into engagement by looping that fastening element over the other distal end.

According to some embodiments, the fastening device 104 can include a feature that provides a suitable structure to attach a padlock that prevents the fastening device from being opened when the padlock is secured to the attachment structure. For example the first distal end 123 can include a first opening designed to receive a shackle of a padlock and the second distal end 124 can include a second opening designed to receive the shackle. According to one embodiment, the first opening and the second opening can extend in a direction perpendicular to a longitudinal axis of the safety device 100. In operation, the distal ends 123, 124 are moved proximate to one another such that the two openings are aligned. The shackle is then slid through the two openings and the padlocked is closed to lock it. The preceding effectively secures the first wall 118 to the second wall 119 and places the fastening device in the closed position. The power cord 140 can be effectively locked to the safety device 100 in this embodiment. In other embodiments illustrated herein, conventional hand tools can be employed to secure the fastening device in the closed position.

According to the illustrated embodiment, a cavity 115 is formed in a central region of the fastening device 104. The cavity 115 has a width W2 and a length L2. The width W2 is an interior dimension measured between the first wall 118 and the second wall 119 with the fastening device 104 in the closed position. The length L2 is an interior dimension measured between the face 106 and distal ends 123, 124 with the fastening device 104 in the closed position.

Referring now to FIG. 3C, further details of the fastening device 104 are illustrated in a rear view provided in the direction in which the power cord 140 is plugged into the safety device 100. FIG. 3C illustrates the fastening device in the closed position. According to this embodiment, an opening 122 is formed between the first distal end 123 and the second distal end 124 with the fastening device 104 closed. The opening includes an inside diameter ID1 located to capture the cord 138 in the opening when the fastening device 104 is closed.

Each of the cavity 115 and the opening 122 are sized and configured to allow the fastening device 104 to receive the power cord 140 and fasten the power cord 140 to the safety device 100 when the power cord is plugged into the female socket 108. For example, the width W2 of the cavity 115 is sized relative to the width W1 of the plug 136 to allow the cavity 115 to receive the plug 136 while still allowing the fastening device 104 to close and fasten to the power cord 140. Similarly, the length L2 of the cavity 115 is sized relative to the length L1 of the plug 136 to allow the cavity 115 to receive the plug 136 and allow the fastening device 104 to close thereby allowing the fastening device 104 to secure the safety device 100 the power cord 140. In addition to the preceding, a shape of the cavity 115 is also selected to accommodate the plug 136 within the fastening device 104 with the fastening device in the closed position. For example, in the illustrated embodiment, the first wall 118 and the second wall 119 each include a taper that brings the two walls together at the distal end. In one embodiment, the taper of the two walls 118, 119 is shaped to conform to the taper found at a transition from the plug 136 to the cord 138 of the power cord 140.

The ID1 of the opening 122 is sized to allow the cord 138 included in the power cord 140 to extend outside the cavity 115. According to the illustrated embodiment, the ID1 of the opening 122 is sized slightly larger than the OD1 of the cord 138. A proper sizing of the ID1 of the opening 122 relative to the OD1 of the cord 138 also allows the first distal end 123 and the second distal end 124 to meet properly to secure the two ends together with the fastening device 104 in the closed position.

To provide wide adaptability, the dimensions (W2, L2) and shape of the cavity 115 can be provided based on the dimensions and shapes of the power cords found in certain types of equipment (for example, vacuums) or the dimensions and shapes of power cords found in a particular brand of power tool. Electrically-operated hand tools are generally operated using 120 VAC circuits rated at 15 or 20 Amps. The conductor size and insulation ratings of the power cords are standardized based on the operating voltage and current ratings of the power source and the power requirements of the tool. Consequently, the ID1 of the opening 122 can be sized and adapted to receive a cord having an OD most often employed among common hand tools.

In operation, the fastening device 104 is placed in the open position by spreading the first wall 118 apart from the second wall 119, for example, as shown in FIG. 1. The power cord 140 is then positioned to align the set of conductors 139 with the female socket 108 and the power cord 140 is plugged into the safety device 100 to bring the face 106 into contact with the face 141. The first wall 118 and the second wall 119 are then moved together to bring the first distal end 123 into contact with the second distal end 124. With the first distal end 118 attached to the second distal end 119 the plug 136 is secured within the cavity 115 and the cord 138 extends through the opening 122.

While the illustrated embodiment, shows that the top and bottom of the cavity 115 are open other approaches can be used. For example, the first wall 118 and the second wall 119 can each wrap 180 degrees around the cavity 115. According to this embodiment, an internal diameter provided by the cavity is sized to receive ad fully enclose the plug 136 when it is plugged in the female socket 108 and the fastening device 104 is in the closed position.

Figure 4A:
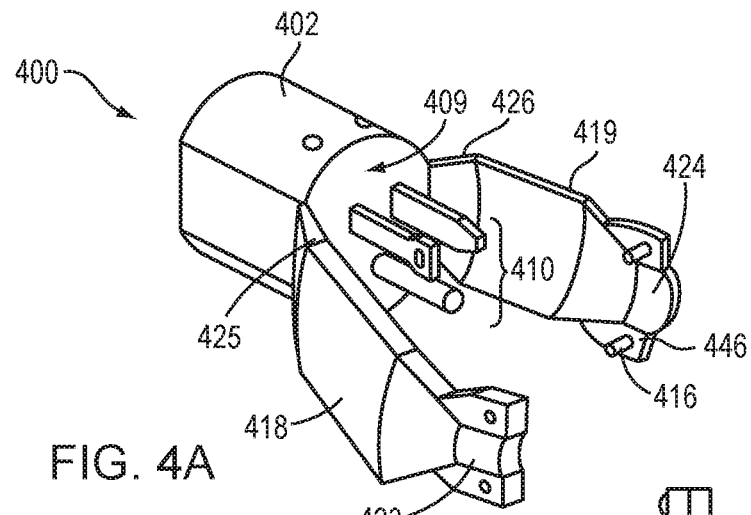
FIGS. 4A-4C illustrate different views of a safety device according to another embodiment.
Figure 4B:
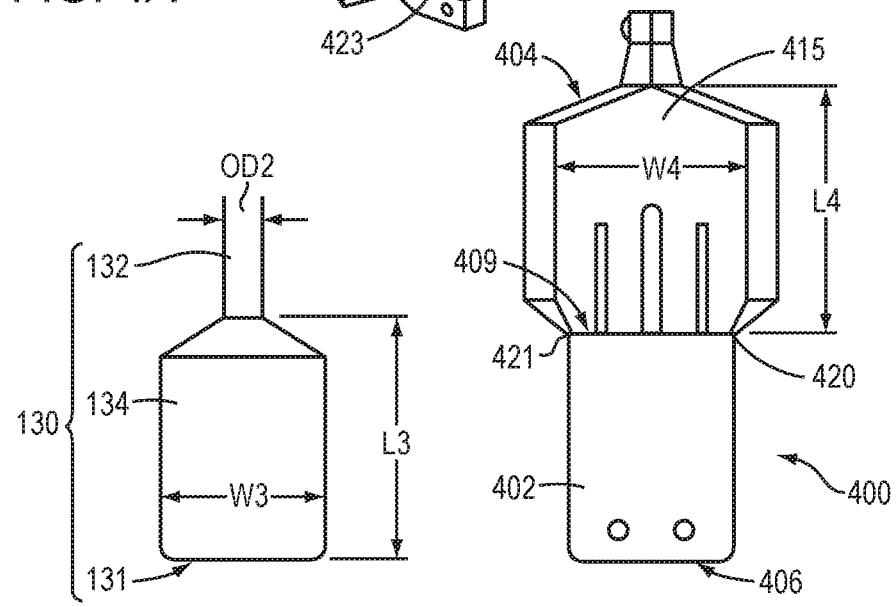
Figure 4C:
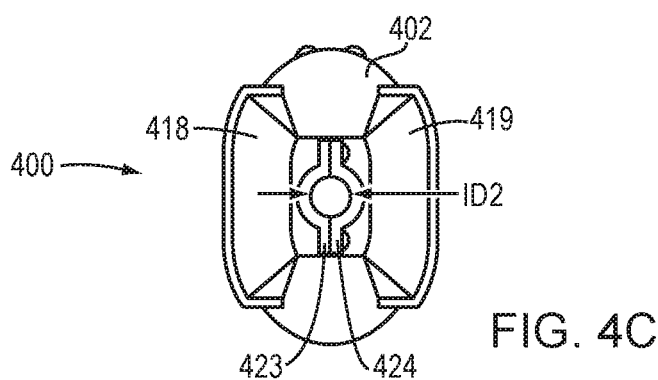

FIGS. 4A-4C illustrate another embodiment of a safety device 400. A difference between the embodiment illustrated in FIGS. 4A-4C and the embodiment illustrated in FIGS. 3A-3C is that the fastening device of the safety device 400 is oriented and configured to fasten to the distal end of the extension cord 130. In many other respects, the features of the safety device 400 are similar to those found in the safety device 100. As a result, some of the features and functionality common to each embodiment are not repeated in full in the following description.

The safety device 400 includes a body 402, a fastening device 404, a first face 406 and a second face 409. A female socket is located in the first face 406. The body 402 includes a second face 409 located at an end of the body opposite the first face 406. A male plug 410 extends from the second face 409. The fastening device 404 includes a first wall 418 including a distal end 423 and a proximate end 425. The fastening device 404 also includes a second wall 419 including a distal end 424 and a proximate end 426. The proximate end 425 of the first wall 418 is coupled to the body 402 at a first hinge 420. The proximate end 426 of the second wall 419 is coupled to the body 402 at a second hinge 421. The distal end 423 includes first fastening structure 444. The distal end 424 includes second fastening structure 446. In the illustrated embodiment, the fastening device includes a pair of fasteners 416, for example, screws or bolts. According to this embodiment, the first fastening structure 444 includes a pair of threaded holes sized and configured to receive the pair of fasteners 416 in a threaded engagement. Further, the second fastening structure 446 includes unthreaded holes sized and configured to allow the pair of fasteners 416 to slide through the holes. According to alternate embodiments, other fastening structure can be used as described above concerning the safety device 100, for example, snaps or clips integral to the walls 418, 419, or additional hardware to assist in maintaining the fastening device in the closed position. Conductors internal to the body 402 connect the conductors located in the female socket (not illustrated) to the conductors located in the male plug 410.

Referring now to FIG. 4B, a top view of the safety device 400 and the extension cord 130 are illustrated with the device 400 and the extension cord 130 located in positions adjacent to one another. The extension cord 130 includes a face 131 located at a distal end of the cord 130. The conductors included in the extension cord 130 are accessible in the face 131 of the female socket 134. For example, the female socket 134 can include a line conductor, a neutral conductor and a ground conductor arranged in a conventional layout that allows the socket 134 to receive conductors provided by the male plug 410. The female socket 130 includes dimensions including a width W3 and a length L3. The cord 132 includes an outside diameter OD2.

According to the illustrated embodiment, a cavity 415 is formed in a central region of the fastening device 404. The cavity 415 has a width W4 and a length L4. The width W4 is an interior dimension measured between the first wall 418 and the second wall 419 with the fastening device 404 in the closed position. The length L4 is an interior dimension measured between the face 406 and distal ends 423, 424 with the fastening device 404 in the closed position.

Referring now to FIG. 4C, further details of the fastening device 404 are illustrated in a rear view provided in the direction in which the safety device 100 is plugged into the extension cord 130. FIG. 4C illustrates the safety device 400 with the fastening device 404 in the closed position. According to this embodiment, an opening 422 is formed between the first distal end 423 and the second distal end 424 with the fastening device 404 closed. The opening 422 includes an inside diameter ID2 located to capture the cord 132 in the opening when the fastening device 404 is closed.

Each of the cavity 415 and the opening 422 are sized and configured to allow the fastening device 404 to receive the extension cord 130 and fasten the extension cord 130 to the safety device 400 when the safety device 400 is plugged into the female socket 134. For example, the width W4 of the cavity 115 is sized relative to the width W3 of the female socket 134 to allow the cavity 415 to receive the socket 134 while still allowing the fastening device 404 to close and fasten to the extension cord 130. Similarly, the length L4 of the cavity 415 is sized relative to the length L3 of the female socket 134 to allow the cavity 415 to receive the socket 134 and allow the fastening device 404 to close thereby allowing the fastening device 404 to secure the safety device 400 the extension cord 130. In addition to the preceding, a shape of the cavity 415 is also selected to accommodate the socket 134 within the fastening device 404 with the fastening device in the closed position. For example, in the illustrated embodiment, the first wall 418 and the second wall 419 each include a taper that brings the two walls together at the respective distal ends. In one embodiment, the taper of the two walls 418, 419 is shaped to conform to the taper found at a transition from the socket 134 to the cord 132 of the extension cord 130.

The ID2 of the opening 122 is sized to allow the cord 132 included in the extension cord 130 to extend outside the cavity 415. According to the illustrated embodiment, the ID2 of the opening 422 is sized slightly larger than the OD2 of the cord 132. A proper sizing of the ID2 of the opening 422 relative to the OD2 of the cord 132 also allows the first distal end 423 and the second distal end 424 to meet properly to secure the two ends together with the fastening device 404 in the closed position.

To provide wide adaptability, the dimensions (W4, L4) and shape of the cavity 415 can be provided based on the dimensions and shapes of the most widely available extension cords, for example, 20 Amp, 120 VAC extension cord carried at one or more box stores found nationally. The conductor size and insulation ratings of the extension cords are standardized based on the operating voltage and current ratings of the power circuits typically found in home, and at commercial and industrial sites. This standardization allows the ID2 of the opening 122 to be sized and adapted to receive a cord having an outside diameter most often found among common extension cords.

In operation, the fastening device 404 is placed in the open position by spreading the first wall 418 apart from the second wall 419. The extension cord 130 is then positioned to align the female socket 134 with male plug 410 and the safety device 400 is plugged into the female socket 134 to bring the face 409 into contact with the face 131. The first wall 418 and the second wall 419 are then moved together to bring the first distal end 423 into contact with the second distal end 424. With the first distal end 418 attached to the second distal end 419 the female socket 134 is secured within the cavity 415 and the cord 132 extends through the opening 422.

One advantage to the embodiment illustrated in FIGS. 4A-4C is that the safety device 400 can provide a universal approach suitable to any of a wide variety of extension cords. Once attached to the distal end of the extension cord 130, the safety device 400 is easily moved about a job site as a part of the extension cord 130. Because the safety device 400 becomes a functional part of the extension cord 130 once attached, the device 400 can be employed with any electrically-powered piece of equipment that is being plugged into the extension cord 130. That is, the safety device 400 does not become tied up with a single piece of equipment. Instead, so long as the safety device remains secured to the female plug 134, the safety device 400 is automatically employed with each new piece of equipment that is plugged into the extension cord 130.

In addition, the attachment of the safety device 400 at the distal end of the extension cord 130 also places the device 400 in close proximity to the user. This helps insure that the safety device 400 is in close proximity to the safety glasses 150. The close proximity assists the continuity of the wireless communication between the safety device 400 and the safety glasses 150. The preceding is especially advantageous when compared with an alternative safety device that is located at the proximate end of the extension cord 130 and/or at the socket where the cord 130 is plugged-in.

Figure 5:
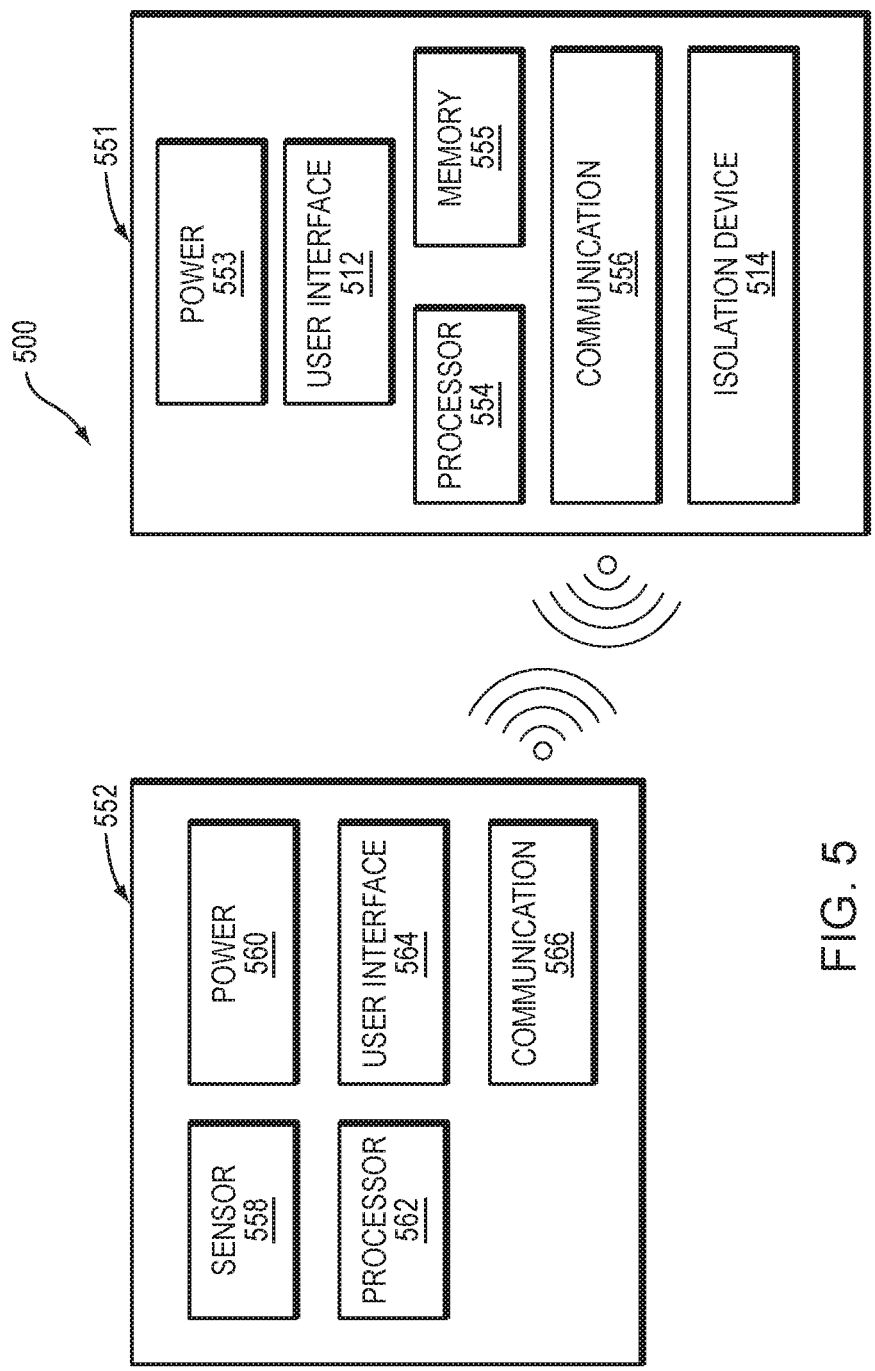
FIG. 5 illustrates an electronic system in accordance with one embodiment.

Referring now to FIG. 5, an electronic system 500 is illustrated in accordance with some embodiments. The electronic system 500 includes a first electronic apparatus 551 configured for inclusion in the safety device 100, 400 and a second electronic apparatus 552 configured for inclusion in the safety glasses 150. For example, the first electronic apparatus can be located in the body 102, 402 of safety device with the second electronic apparatus 552 included as a part of the safety glasses 150. In general, the electronic system 500 provides for: sensing of a status of the safety glasses (for example, whether they are being worn properly); operation of an isolation device to maintain an electrical output in an off state unless the glasses are being worn properly; and wireless communication between the first electronic apparatus 551 and the second electronic apparatus 552. As described herein, additional or alternate features and functionality of the electronic system 500 can vary depending on the embodiment.

According to the illustrated embodiment, the first electronic apparatus 551 includes a user interface 512, an isolation device 514, a power system 553, a processor 554, a memory 555 and a communication module 556. The second electronic apparatus 552 includes a sensor 558, a power system 560, a processor 562, a user interface 564 and a communication module 566. Each of the first electronic apparatus 551 and the second electronic apparatus 552 include respective power circuits (not illustrated). For example, the components included in the first electronic apparatus 551 can be coupled to the power system 553 by one or more power buses or lines. The power buses are employed to deliver the necessary power to the various illustrated components and to other components included in the device depending on the embodiment. The components included in the second electronic apparatus 552 can be coupled to the power system 560 in a similar fashion.

Each of the first electronic apparatus 551 and the second electronic apparatus 552 also include respective communication circuits (not illustrated). For example, the components included in the first electronic apparatus 551 can be coupled by one or more communication buses or signal lines. The communication buses can be used for the communication of instructions/commands and data between the illustrated components and between the illustrated components and other components included in the device depending on the embodiment. The components included in the second electronic apparatus 552 can be coupled by one or more communication buses or signal lines included in the apparatus 552 in a similar fashion.

In some embodiments, the isolation device 514 operates in the manner described above concerning the isolation device 114. For example, depending on the embodiment, the isolation device 514 can operate to open and close one or more conductors included in the body 102, 402. When open, the isolation device prevents current flow between the female socket 108, 408 and the male plug 110, 410 included in the safety device 100, 400. The isolation device closes when the safety device 100, 400 receives a signal that indicates the safety glasses 150 are being worn properly. The isolation device 514 can be implemented using any of a variety of technologies depending on the embodiment and provided that the isolation device is rated for the operating voltage and current required for a particular application, for example, a 120 VAC, 20 Amp circuit. According to one embodiment, the isolation device 514 includes a mechanical switch including contacts that make and break the conductor in which the device 514 is installed. According to an alternate embodiment, the isolation device 514 includes an electronic switch that operates to block current flow, for example, when the isolation device 514 is in the off state.

The communication module 556 can also be implemented using any of a variety of technologies depending on the embodiment provided that the module 556 supports wireless communication with the second electronic apparatus 552. For example, the communication module 556 can employ one of either RF communication or optical communication in different embodiments. According to one embodiment, a Bluetooth™ protocol is employed by the communication module 556. Such a protocol or a similar technology is well suited to the wireless communication employed by the system 500 because the first electronic apparatus 551 and the second electronic apparatus 552 are typically separated by a small distance and the amount of data transmitted between the two devices is typically not large. According to one embodiment, a Bluetooth™ protocol is implemented with an automatic pairing of the first electronic apparatus 551 and the second electronic apparatus 552. For example, the automatic pairing can be completed independent of any action by the user other than turning on either or both of the first electronic apparatus 551 and the second electronic apparatus 552. The preceding approach is advantageous in a retail setting where, for example, a system (for example, the system 200) including each of the safety device 100, 400 and the safety glasses 150 can be packaged and sold together to an end consumer. Once the system is purchased, the user need only remove the system from the packaging and turn on the system to use the safety device. The approach is also advantageous in situations where multiple users are located on the same job site because it helps ensure that the user and their associated safety device 100, 400 are in communication with the associated pair of safety glasses.

According to various embodiments, the communication module 556 includes one or more of a USB port or other hardware serial communication in combination with the capability to employ one or more wireless communication protocols such as an optical communication protocol, a Bluetooth™ communication protocol or a Wi-Fi communication protocol. In one embodiment, the communication module 556 provides for wireless communication between the first electronic apparatus 551 and an external device such as a tablet computer or mobile phone.

In various embodiments, the power system 553 is employed to provide operating power for the safety device 100, 400. For example, operating power can be provided for operating one or more of the components included in the first electronic apparatus 551 such as the isolation device 514, the processor 554, and the communication module 556 as some examples. The power system 553 can include any of a power source, power conversion circuitry and power conditioning circuitry. In some embodiments, the power system 553 includes a battery power source, for example, one or more coin cell batteries, alkaline batteries or lithium batteries. According to another embodiment, the power system 553 is employed to convert power provided from a line conductor included in the body 102, 402. In either approach, power conversion circuitry can be included to convert the power provided from the power source to a nominal voltage and/or current required by the components included in the first electronic apparatus 551.

Depending on the embodiment, the processor 554 and the memory are included in a microcontroller. According to another embodiment, the processor 554 is included in the microcontroller along with memory 555 including either or both of RAM and ROM. In a further embodiment, the memory 555 also includes memory external to microcontroller. In other embodiments, the processor can be included in a microprocessor. According to one embodiment, the first electronic apparatus 551 includes one or more integrated circuits.

The user interface 512 can vary depending on the embodiment as described above concerning the user interface 112 illustrated in FIG. 1. For example, the user interface 512 can include one or more indicating lamps, switches or pushbuttons or audio speakers. In one embodiment, the user interface includes a display, for example, an LCD display that can display the state/status of the various features and functionality included in the safety device 100, 500 in which the first electronic apparatus 551 is installed.

The sensor 558 included in the second electronic apparatus 552 can employ different types of technology depending on the embodiment. In various embodiments, a pressure sensitive switch is included in the sensor 558 to sense contact between the users head, face or nose when the safety glasses are being worn by the user. According to one embodiment, a mechanical switch is employed. According to another embodiment, a piezoelectric switch is employed. According other embodiments, the sensor 558 includes a physiological-monitoring sensor. For example, the sensor 558 can employ a capacitive sensor to determine whether the safety glasses are in contact with the skin of the user. A pulse or skin temperature sensor can be used in other embodiments. Further, the sensor 558 can include a single sensor, multiple sensors of the same type or multiple different-types of sensors depending on the embodiment. According to further embodiments, the sensor 558 can include one or more inertial sensors. For example, the sensor 558 can include one or more accelerometers employed to detect an orientation and/or relative motion of the safety glasses 550. In one embodiment, the sensor 558 includes a multi-axis accelerometer to determine the orientation of the safety glasses relative to the orientation of the user.

The communication module 566 included in the second electronic apparatus 552 can also be implemented using any of a variety of technologies depending on the embodiment provided that the module 566 supports wireless communication with the first electronic apparatus 551. For example, the communication module 566 can employ one of either RF communication or optical communication in different embodiments. According to one embodiment, a Bluetooth™ protocol is employed by the communication module 566. As mentioned above concerning the communication module included in the first electronic apparatus 551, automatic pairing can be employed in some embodiments to improve the user's experience and better ensure that the safety device 100, 400 is effectively employed.

The user interface 564 can vary depending on the embodiment. For example, the user interface 564 can include one or more indicating lamps, switches or pushbuttons or audio speakers. Due to the size constraints of the second electronic apparatus 552, the scale and functionality of the user interface 564 may be more limited than that found in the user interface 512 included in the first electronic apparatus 551. According to one embodiment, the second electronic apparatus 552 does not include the user interface 564. According to another embodiment, the user interface 564 only includes one or more indicating lamps, for example, to provide the user with information concerning whether the wireless communication module 566 is operational.

In various embodiments, the power system 560 is employed to provide operating power for the second electronic apparatus 552. For example, operating power can be provided for operating one or more of the components included in the second electronic apparatus 552 such as the processor 554, and the communication module 556 as two examples. The power system 560 can include any of a power source, power conversion circuitry and power conditioning circuitry. In some embodiments, the power system 560 includes a battery power source, for example, one or more coin cell batteries, alkaline batteries or lithium batteries. According to some embodiments, power conversion circuitry can be included to convert the power provided from the power source to a nominal voltage and/or current required by the components included in the second electronic apparatus 552. According to one embodiment, the second electronic apparatus 552 is a passive device (for example, a passive RFID device) that does not include the power source 560.

Depending on the embodiment, the processor 562 can be a standalone component (for example, a microprocessor) or included in a microcontroller. According to either embodiment, the second electronic apparatus 552 can include memory, for example, RAM, ROM or a combination of both RAM and ROM.

According to various embodiments, the second electronic apparatus 552 is provided in a form factor that is small enough to allow the apparatus 552 to be integrated into the safety glasses 150 without interfering with their use. For example, users often have a negative view of personal protective equipment (glasses, gloves, respirators, etc.) because they can increase the difficulty in completing a task. Thus, the second electronic apparatus 552 must be small enough to avoid a negative impact on the perceived comfort and utility of the safety glasses 150 in which the second electronic apparatus 552 is employed. The size and functionality of the components included in the second electronic apparatus 552 can be selected with the preceding in mind to maintain the small profile and form factor required of the apparatus 552. Further, although the second electronic apparatus 552 is illustrated as a single element including different components (i.e., the sensor 558, the processor 562, etc.), one or more of the identified components or other components included in the second electronic apparatus 552 can be located at a first region of the safety glasses 150 while another component or components included in the second electronic apparatus 552 can be located at a second region of the safety glasses 150.

Safety glasses can sometimes be damaged during normal use such that they have to replaced. According to one embodiment, the second electronic apparatus 552 is detachable from the safety glasses 150 either in whole or part. For example, the second electronic apparatus 552 can be fastened to a first pair of safety glasses in a manner that allows the second electronic apparatus 552 to be removed and re-fastened to a second pair of safety glasses if the first pair of safety glasses becomes unusable.

According to some embodiments, the system 500 includes an RFID system where, for example, the first electronic device 551 interrogates the second electronic device 552 to determine the status of a particular pair of safety glasses, i.e., whether the glasses are being worn properly. According to one embodiment, the second electronic apparatus 552 is a battery assisted RFID tag. In one alternate embodiment, the second electronic apparatus 552 is a semi-active RFID tag. In still another alternate embodiment, the second electronic apparatus 552 is an active RFID tag.

Figure 6:
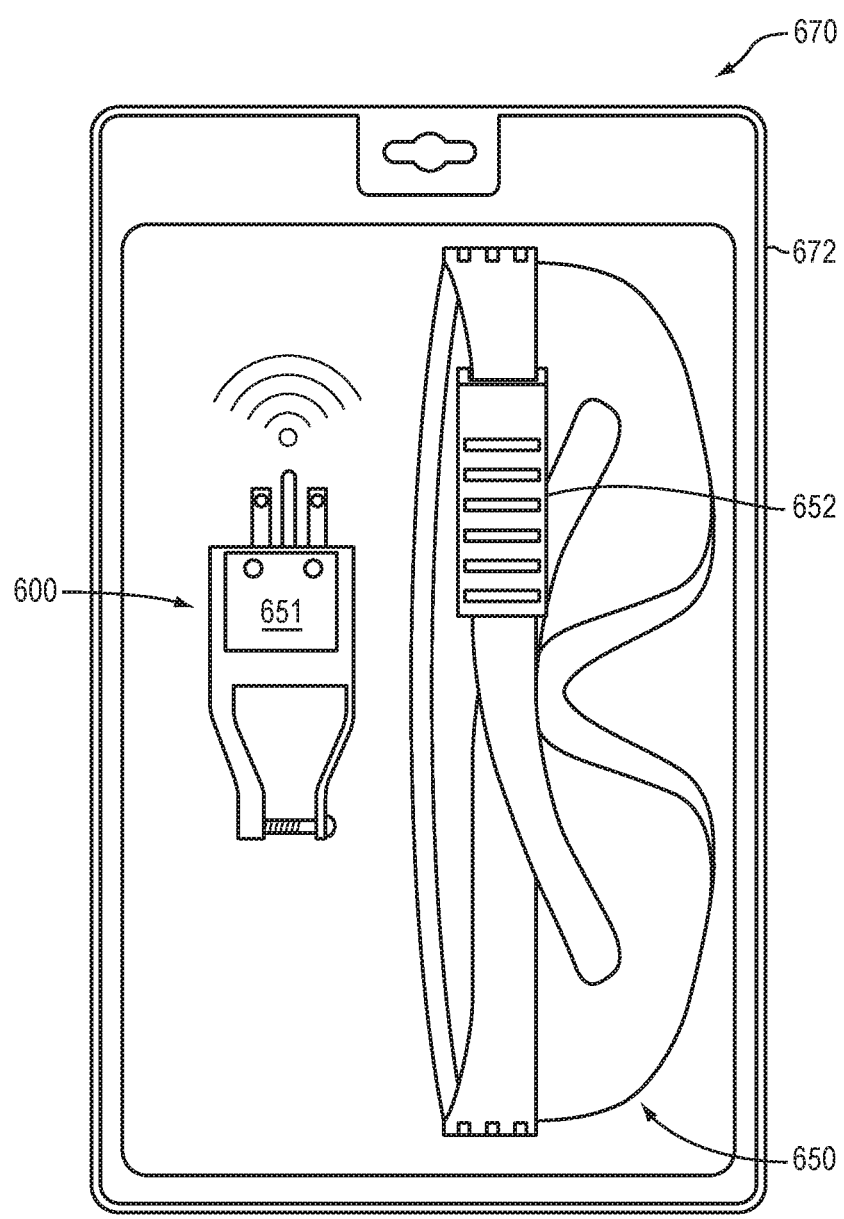
FIG. 6 illustrates a safety kit in accordance with one embodiment.

Referring now to FIG. 6, a safety kit 670 is illustrated in accordance with one embodiment. The safety kit 670 includes a product package 672, a safety device 600, and safety glasses 650. According to the illustrated embodiment, a first electronic system 651 is included in the safety device 600 and a second electronic system 652 is included as a part of the safety glasses 650. In the illustrated embodiment, each of the safety device 600 and the safety glasses 650 are enclosed in the package 672.

According to some embodiments, the product package 672 is configured for display at a point of sale location, for example, for display on a rack or shelf viewed by shoppers in a retail store. In one embodiment, all or a portion of the product package 672 is transparent. Transparent packaging allows the shoppers to easily view the safety items included in the package to quickly ascertain the nature of the contents included therein. For example, with the safety device 600 and the safety glasses 652 visible to individuals passing by the display, shoppers will readily understand that the combination provides an eye-safety solution in combination with an electrical isolation device. Although FIG. 6 illustrates the product package 672 in the form of a blister pack other forms of packaging can be used depending on the embodiment. According to one embodiment, the safety device 600 and the safety glasses 652 are packaged in cardboard packaging including a transparent window. According to another embodiment, the safety device 600 and the safety glasses 652 are packaged in non-rigid transparent packaging, for example, a plastic bag. According to still another embodiment, the safety device 600 and the safety glasses 652 are packaged in the product package 672 and are not visible without opening the package 672.

According to various embodiments, the first electronic apparatus 651 includes components, features and functionality as described for the various embodiments of the first electronic apparatus 551 illustrated in FIG. 5. Further, depending on the embodiment, the second electronic apparatus 552 can include components, features and functionality as described for the various embodiments of the second electronic apparatus 552 illustrated in FIG. 5. In general, the safety device 600 and safety glasses 650 operate to maintain electrical isolation of equipment plugged into the safety device 600 until the safety glasses 650 are being worn properly by the user.

Depending on the embodiment, the safety device 600 can provide an apparatus that is configured to secure to the distal end of a cord employed with electrically-operated equipment, (for example, the safety device 100) or at the distal end an extension cord (for example, the safety device 400). Various embodiments can provide a "universal" solution where a cavity (for example, one of the cavities 115, 415) and an opening (for example, one of the openings 122, 422) are sized and adapted to allow the safety device 650 to be employed with the most common range of physical sizes and electrical ratings of cords employed with utilization equipment and extension cords, respectively. According to these embodiments, the safety device can be easily secured to a first piece of equipment while that piece of equipment is being used and then removed and attached to the power cord of a second piece of equipment when the second piece of equipment is being used.

Figure 7:
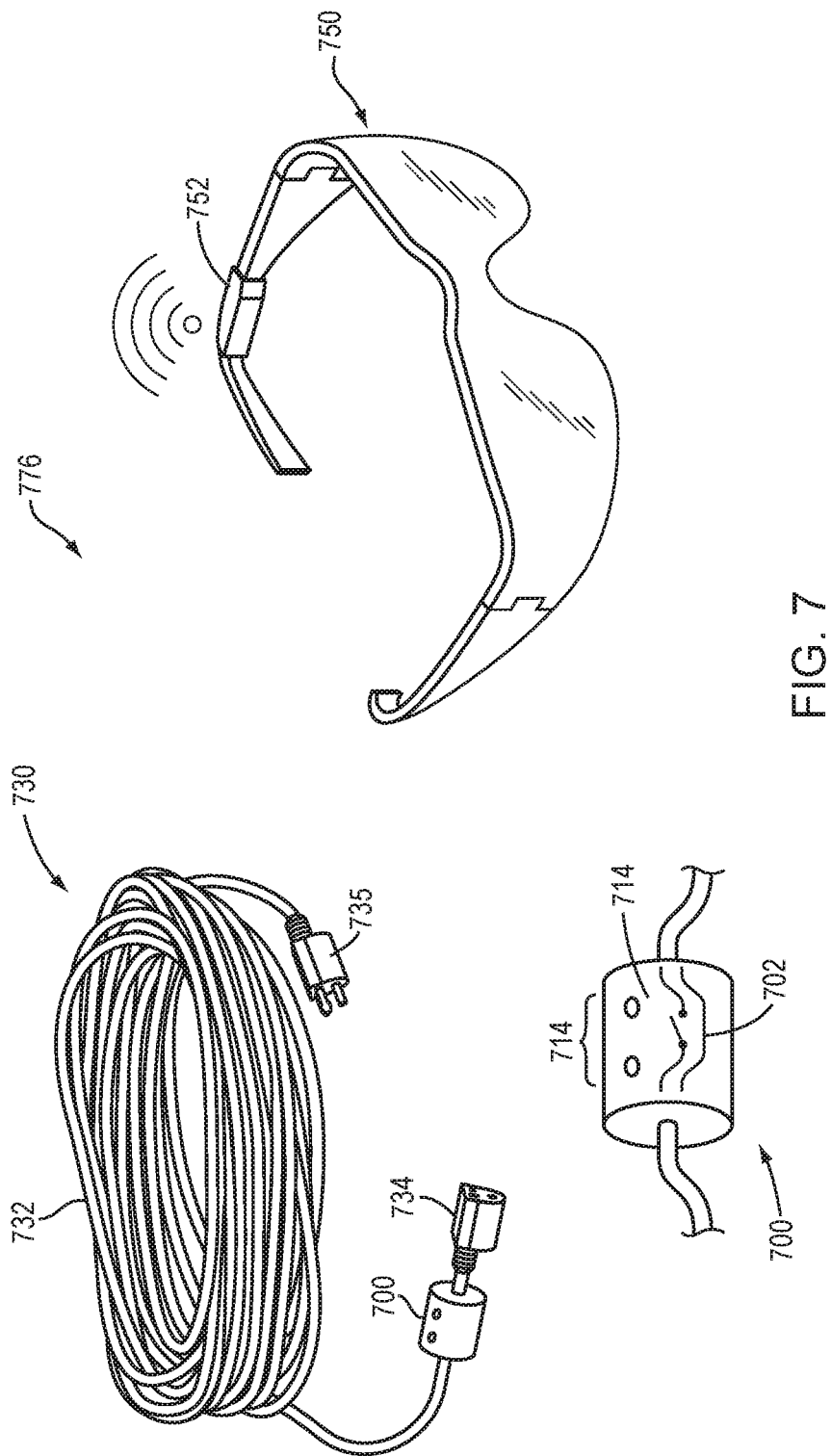
FIG. 7 illustrates a safety system in accordance with another embodiment.

Referring now to FIG. 7, a safety system 776 is illustrated in accordance with one embodiment. The safety system 776 includes a safety device 700, safety glasses 750 and an extension cord 730 including a power cord 732, a distal end 734 and a proximate end 735. The safety device 700 includes a body 702 that houses a user interface 712 and an isolation device 714. The safety glasses 750 include an electronic apparatus 752. In general, the safety device 700 and safety glasses 750 operate to maintain electrical isolation between equipment plugged into the distal end of the safety cord 734 and the proximate end 735 of the safety cord until the safety glasses 750 are being worn properly by the user.

In various embodiments, the safety device 700 is included as an integral part of the extension cord 730, for example, an integral part of an otherwise conventional extension cord. According to some embodiments, the user interface 712 and isolation device 714 are included in an electronic apparatus that includes components, features and functionality as described for the various embodiments of the first electronic apparatus 551 illustrated in FIG. 5. Further, depending on the embodiment, the electronic apparatus 752 can include components, features and functionality as described for the various embodiments of the second electronic apparatus 552 illustrated in FIG. 5.

Because the safety device 700 is an integral component of the extension cord 730, the safety device 700 is automatically employed with any piece of electrically-operated equipment that is powered by the extension cord 730. In addition, it is impractical for a user operating equipment using the extension cord 730 to remove the safety device 700 from the cord 732. Thus, the safety device 700 goes wherever the extension cord 730 is used.

Figure 8:
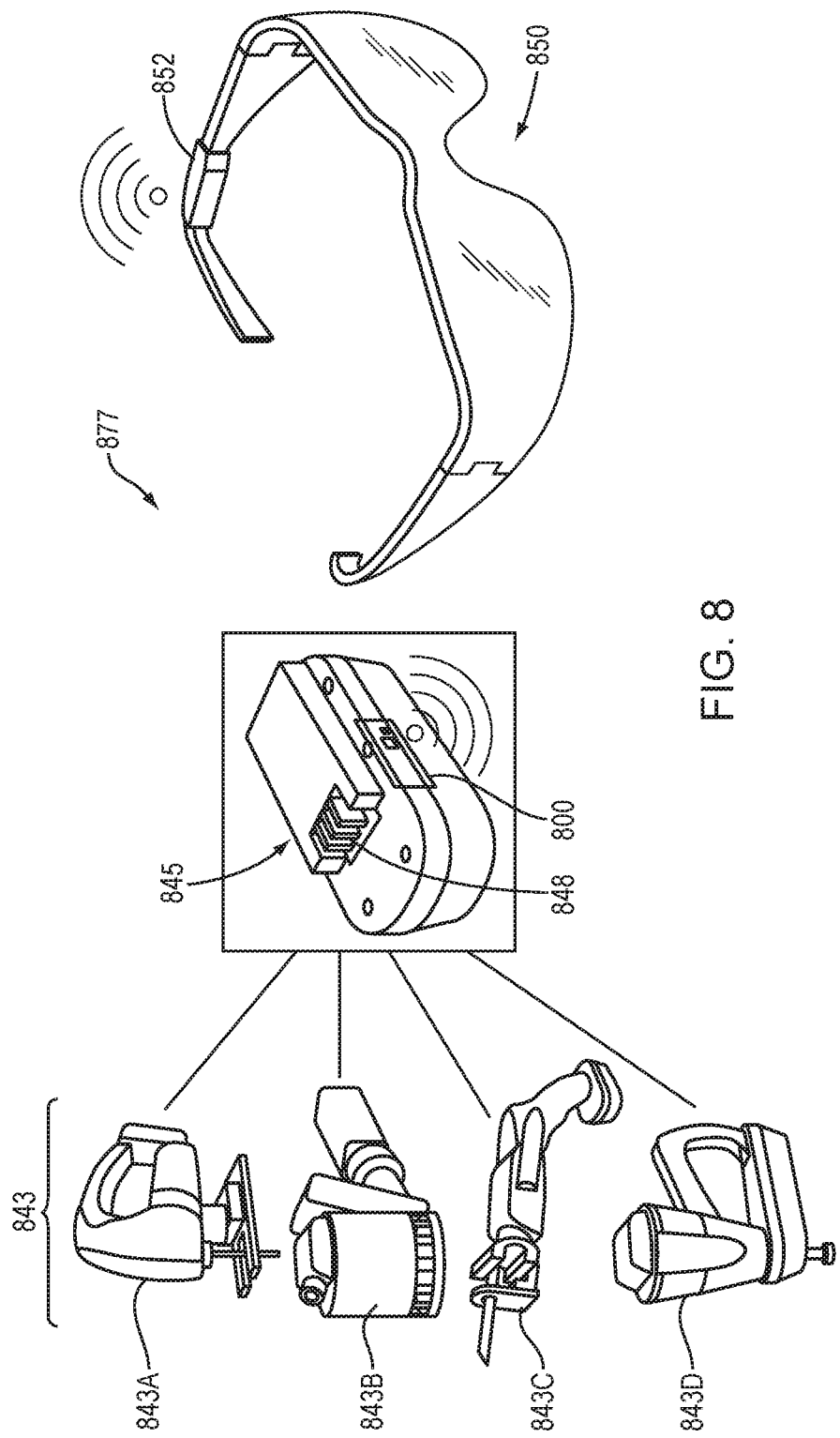
FIG. 8 illustrates a safety system in accordance with yet another embodiment.

Referring now to FIG. 8, a safety system 877 is illustrated in accordance with one embodiment. The safety system 877 includes a safety device 800, safety glasses 850 and battery-operated equipment 843 including a battery pack 845. The battery pack 845 includes terminals 848 that are connected to an electric motor included in the battery-operated equipment 843. In some embodiments, the battery pack 845 is a removable battery pack. The safety glasses 850 include an electronic apparatus 852. In general, the safety device 800 and safety glasses 850 operate to maintain electrical isolation between at least one conductor included in the output of the battery pack 845 and a corresponding input connection to the electric motor until the safety glasses 850 are being worn properly by the user.

The battery-operated equipment 843 can include handheld power tools, for example, a jig saw 843A, a sander 843B, a reciprocating saw 843C and a nail gun 843D. One of ordinary skill in the art in view of the disclosure provided herein will recognize the preceding list is non-exhaustive. Thus, while the illustrated embodiment shows a mix of conventional cordless equipment, other cordless equipment can be employed with the safety device 800, for example, staple guns and drills to name two.

In various embodiments, the safety device 800 is included as an integral part of the battery pack 845. According to some embodiments, the safety device 800 is an electronic apparatus that includes components, features and functionality as described for the various embodiments of the first electronic apparatus 551 illustrated in FIG. 5. For example, the safety device 800 can include an isolation device and a user interface. Further, depending on the embodiment, the electronic apparatus 852 can include components, features and functionality as described for the various embodiments of the second electronic apparatus 552 illustrated in FIG. 5.

According to one embodiment, the battery pack 845 is removed from the battery-operated equipment for recharging via the terminals 848. For example, the battery pack 845 can be placed in a charging station in which the terminals 848 are connected to a source of charging power. Typically, safety glasses are not required for the charging operation. In this embodiment, the isolation device included in the safety device 800 can be temporarily placed in a closed-state to permit current flow from the terminals 848 to the battery included in the battery pack 845 during charging. In one embodiment, the safety device 800 includes a mechanically operated switch that the user moves from a first position in which a user must be properly wearing safety glasses to close the isolation device to a second position in which the isolation device is placed in a closed position regardless of whether the associated pair of safety glasses 850 is worn by the user. According to one embodiment, the switch is inaccessible unless the battery pack 845 is removed from the battery-operated equipment 843. Further, the switch and the housing for the battery pack 845 provided by the battery-operated device can be configured such that it creates a mechanical interference that prevents the battery pack 845 from being reinstalled in the battery-operated equipment 843 unless the switch is located in the first position. According to some embodiments, the safety device 800 automatically changes state to permit current flow for charging when the battery pack is removed from the battery operated equipment 843.

Embodiments of the safety device 800 can be advantageously employed to retrofit battery operated equipment 843 that is provided with a conventional battery pack as originally shipped from the manufacturer. According to these embodiments, a battery pack 845 including the safety device 800 is configured to directly replace the conventional battery pack. The removable nature of the original power source (i.e., the battery pack) allows the retrofit of the battery operated equipment 843 in a ready manner. According to one embodiment, a retrofit battery pack equipped with the safety device 800 is packaged with one or more items of personal protective equipment for sale of the items together with the retrofit battery pack. These systems can be seamlessly deployed together in the field with the safety device 800 and corresponding electronic apparatus 852 paired for immediate use. Thus, worksite safety can be improved at a significant cost savings because there is no need to replace the battery operated equipment itself.

Figure 9:
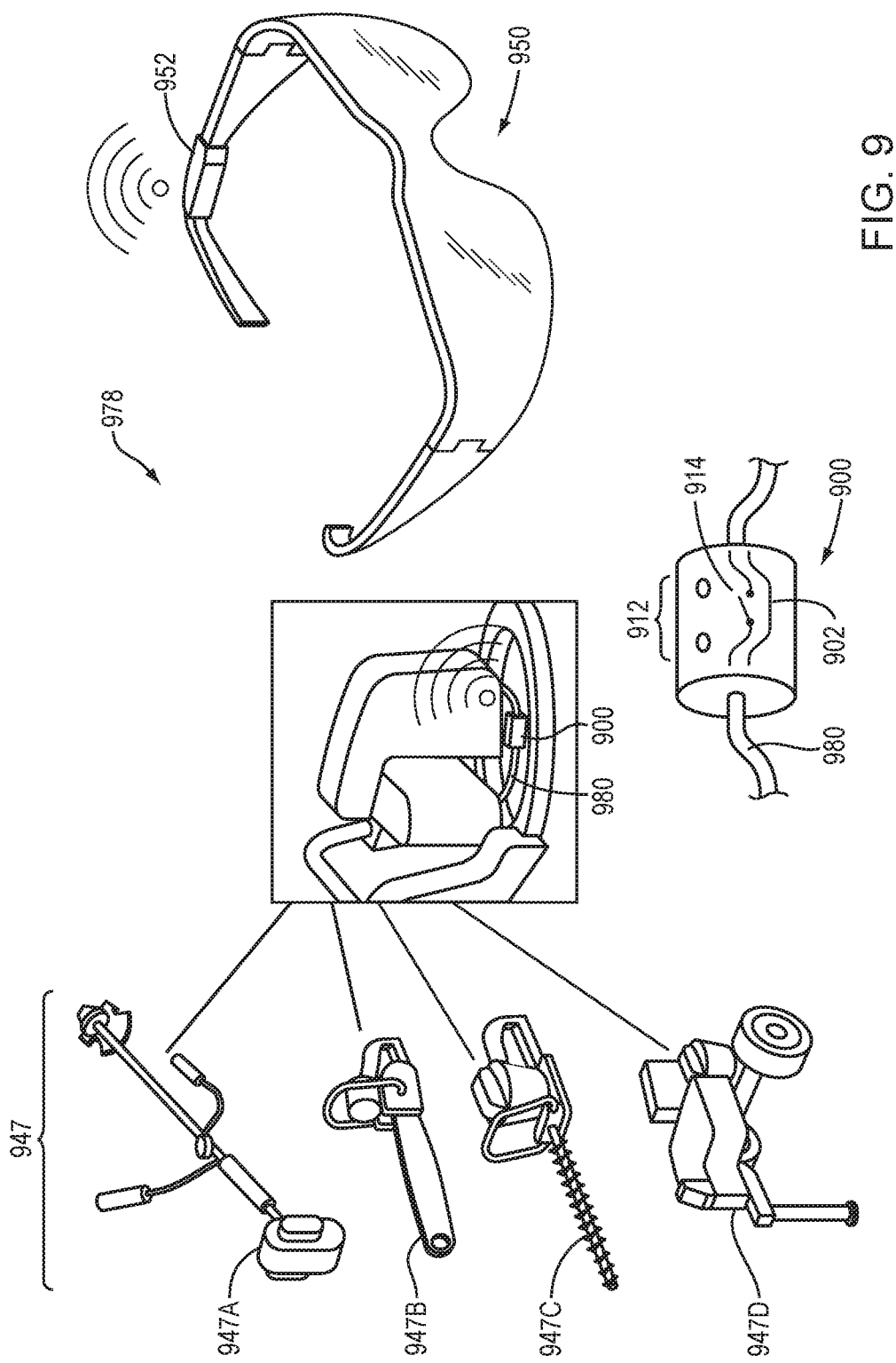
FIG. 9 illustrates a safety system in accordance with still another embodiment.

Referring now to FIG. 9, a safety system 978 is illustrated in accordance with one embodiment. The safety system 978 includes a safety device 900, safety glasses 950 and equipment powered by a combustion engine 947. The equipment powered by the combustion engine 947 includes a spark plug wire 980. The safety glasses 950 include an electronic apparatus 952. In general, the safety device 900 and safety glasses 950 operate to maintain electrical isolation in the spark plug wire until the safety glasses 950 are being worn properly by the user. According to the illustrated embodiment, the safety device 900 includes a body 902 that houses a user interface 912 and an isolation device 914.

The equipment powered by the combustion engine 947 can include, for example, a weed whacker 947A, a chain saw 947B, a hedge trimmer 947C and a log splitter 947D. One of ordinary skill in the art in view of the disclosure provided herein will recognize the preceding list is non-exhaustive. Thus, while the illustrated embodiment shows a mix of equipment 947, other equipment powered by a combustion engine can be employed with the safety device 900 such as lawn mowers and snow blowers as two examples.

In various embodiments, the safety device 900 is included as an integral part of the spark plug wire 980. According to some embodiments, the safety device 900 is an electronic apparatus that includes components, features and functionality as described for the various embodiments of the first electronic apparatus 551 illustrated in FIG. 5. Further, depending on the embodiment, the electronic apparatus 952 can include components, features and functionality as described for the various embodiments of the second electronic apparatus 552 illustrated in FIG. 5.

Figure 10:
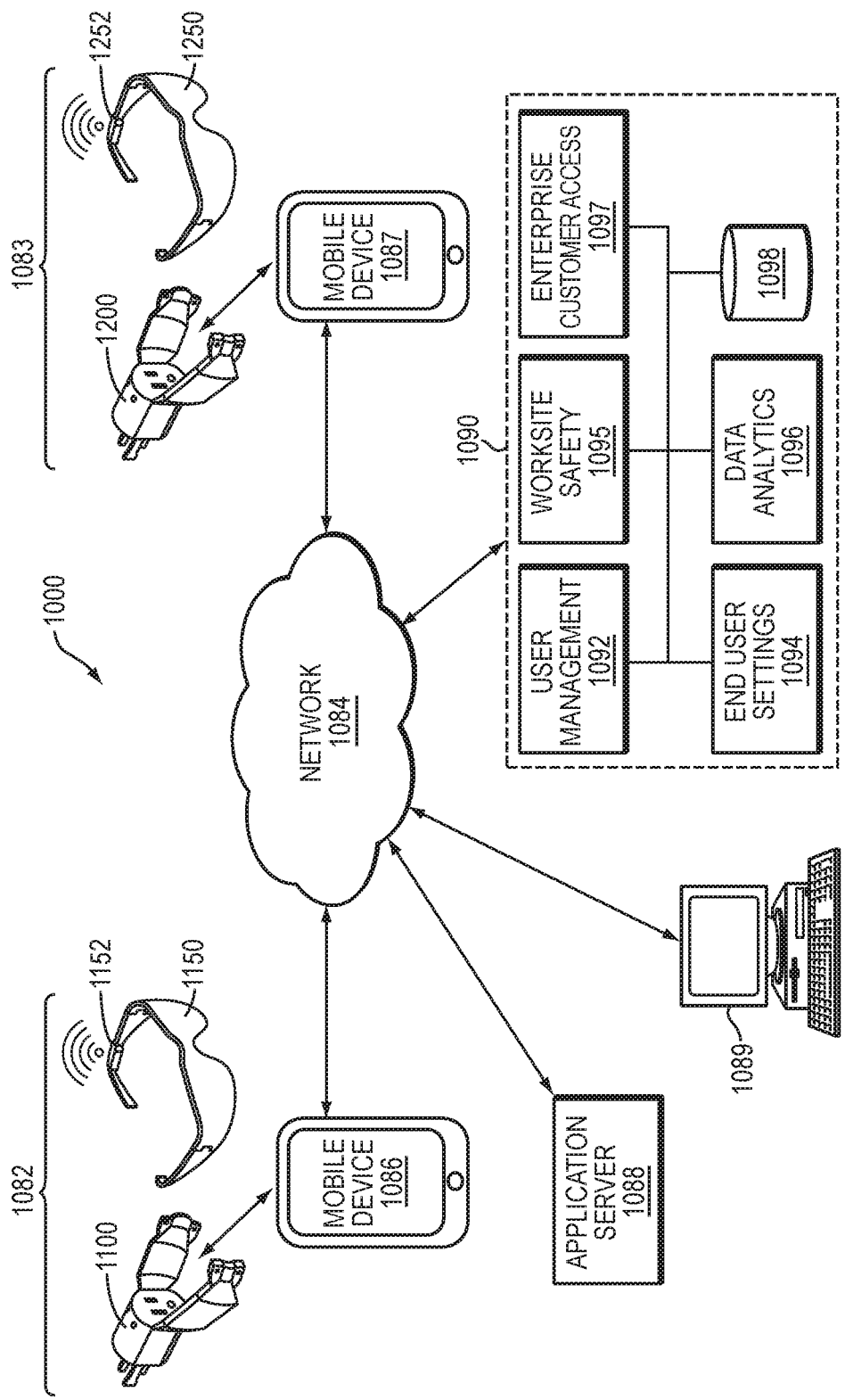
FIG. 10 illustrates a system including a network operating environment for safety systems in accordance with one embodiment.

FIG. 10 illustrates a system 1000 including a network operating environment employed with one or more safety systems. According to the illustrated embodiment, the system 1000 includes a first safety system 1082, a second safety system 1083. a network 1084, a first mobile device 1086, a second mobile device 1087, an application server 1088, an additional user device 1089, and services 1090, for example, services and/or resources remotely accessible by the devices 1086, 1087 and 1089 for use in monitoring and controlling various operations provided by the system 1000. In the illustrated embodiment, the services 1090 include user management 1092, end user settings 1094, worksite safety 1095, enterprise customer access 1097, data analytics 1096 and one or more databases 1098. The services 1090 and resources are described in more detail herein. As should be apparent to one of ordinary skill in the art in view of the disclosure provided herein, the services 1090 can include other services and/or resources and combinations of services and/or resources depending upon the embodiment.

According to the illustrated embodiment, the first safety system 1082 includes a first safety device 1100 and safety glasses 1150 including an electronic apparatus 1152. Further, the second safety system 1083 includes a second safety device 1200 and safety glasses 1250 including an electronic apparatus 1252. Depending on the embodiment, the safety systems 1082, 1083 can operate in a manner as shown and described with reference to any of the preceding embodiments. For example, the safety devices 1100, 1200 can include components, features and functionality as described for the various embodiments of the safety devices 100, 400 and the safety systems 1300, 1600 as illustrated in FIGS. 3, 4, 13 and 16, respectively. For example, the safety systems 1082, 1083 can operate as shown and described with reference to the safety system 200 illustrated in FIG. 2. The safety devices 1100, 1200 include respective electrical isolation devices to maintain an open circuit in one or more line conductors included in the safety device 1100, 1200 to prevent operation of equipment plugged into the device 1100, 1200 unless the electronic systems receives information communicated from the corresponding pair of safety glasses 1150, 1250, respectively, that indicates the safety glasses are being worn properly.

In one embodiment, the first safety device 1100 is associated with a first user and the second safety device is associated with a second user. In one further embodiment, the first user and the second user are located at a single geographic location, for example, at a job site such as a construction site a commercial or industrial facility, a trade show or other location at which a plurality of electrically operated tools and equipment are employed in a dynamic setting. According to this embodiment, the first safety device 1100 is in wireless communication with the safety glasses and the second safety device 1200 is in wireless communication with the safety glasses 1250.

The system 1000 also allows wireless communication between a safety device, for example, safety devices 1100 1200, and a mobile device of a user. According to the illustrated embodiment, the first safety device 1100 is in wireless communication with the first mobile device 1086 and the second safety device 1200 is in wireless communication with the second mobile device 1087. According to these embodiments, the wireless communication can assist parties responsible for workplace safety (for example, employers, property owners, etc.) to remotely monitor the operation and use of the safety systems 1082, 1083. According to one embodiment, Bluetooth™ wireless communication is employed in the communication between the safety device 1100, 1200 and the corresponding mobile device 1086, 1087, respectively.

In various embodiments, the services 1090 are employed by one or more of the end users of the safety systems 1082, 1083 and enterprise customers, for example, insurers, employers and property owners. The user management services 1092 can be employed by end users to create a user account. The end user settings 1094 can be used by the end users to activate location based-features and modify other settings associated with the user by the system 1000. The worksite safety services 1095 can be employed by enterprise customers to remotely monitor the deployment and use of the safety systems 1082, 1083 in the field, for example, at remote job sites. In addition, the worksite safety services 1095 can be employed by enterprise customers to establish workplace safety rules related to the use of the safety systems 1082, 1083. In some embodiments, the workplace safety module, via communication with the end user's mobile device 1086, 1087 can be employed to send notifications to improve worksite safety, for example, in response to data received concerning use of the safety systems 1082, 1083. The data analytics service 1096 can be employed to provide enterprise customers with information to evaluate job-site safety based, at least in part, on the operation of the safety devices 1082, 1083.

According to one embodiment, statistical data concerning the quantity of safety systems employed, the percentage of on-site personnel employing safety systems and the like is stored in the one or more databases 1098 where it is accessed by insurers, employers and/or property owners. In a further embodiment, an API is made available to allow registered third parties to access the statistical data.

According to some embodiments, the one or more databases 1098 store user identification information (for example, user IDs and passwords), operational data concerning a history of use of one or more safety devices 1082, 1083, and worksite safety data. Depending on the embodiment, the database 1098 can include any of a relational database, object-oriented database, unstructured database, or other database. Further, the database 1098 can be included in any aspect of a memory system, such as in RAM, ROM or disc, and may also be separately stored on one or more dedicated data servers included in the services 1090.

In general, the network 1084 can include either or both of local-area networks (LANs), wide area networks (WANs), wireless communication, wired communication and may include the Internet. According to a further embodiment, the network 1084 provides access "over-the-cloud" to one or more remote devices, servers, application resource management and/or data storage systems. For example, the network 1084 can allow communication between any of the first mobile device 1086, the second mobile device 1087, and the other user devices 1089 with one another and/or with any of the other resources and devices coupled to the network 1084. Communication can occur using any of Wi-Fi networks, Bluetooth™ communication, cellular networks, satellite communication, and peer-to-peer networks available either alone or in combination with one another via the network 1084. Other communication protocols and topologies can also be implemented in accordance with various embodiments.

According to various embodiments, the mobile devices 1086, 1087 and the other user devices 1089 can be, for example any of a portable device such as a tablet computer, a hand-held computer, a personal digital assistant, a cellular telephone, a smart phone and/or other processing devices. In one embodiment, the other user devices 1089 include a desktop computer or other device having limited or no mobility but suitable for communicating with other devices, systems and/or resources connected via the network 1084.

Figure 11A:
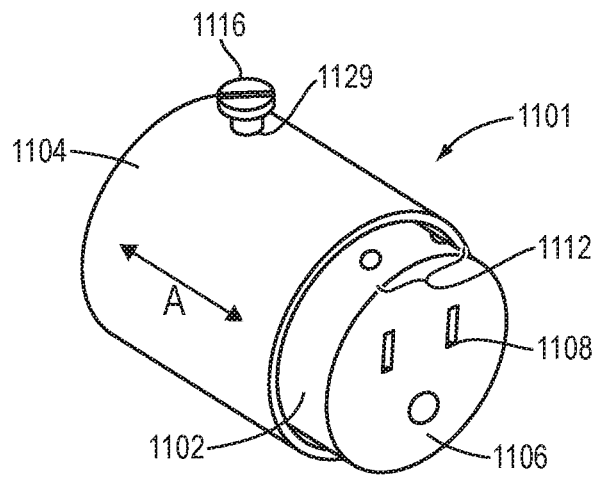
FIGS. 11A-11C illustrate a first component of a safety system in accordance with another embodiment.
Figure 11B:
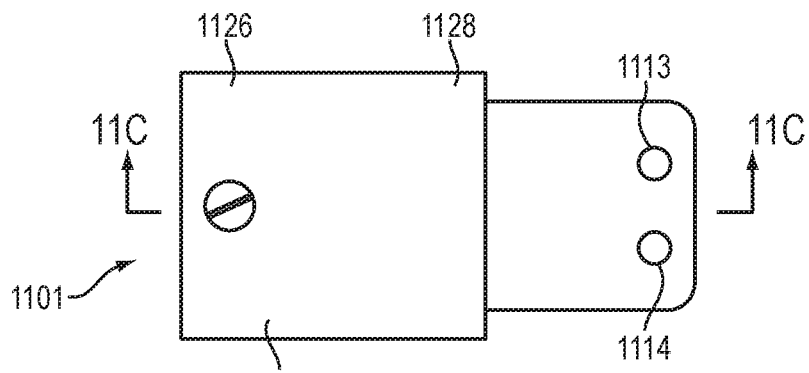
Figure 11C:
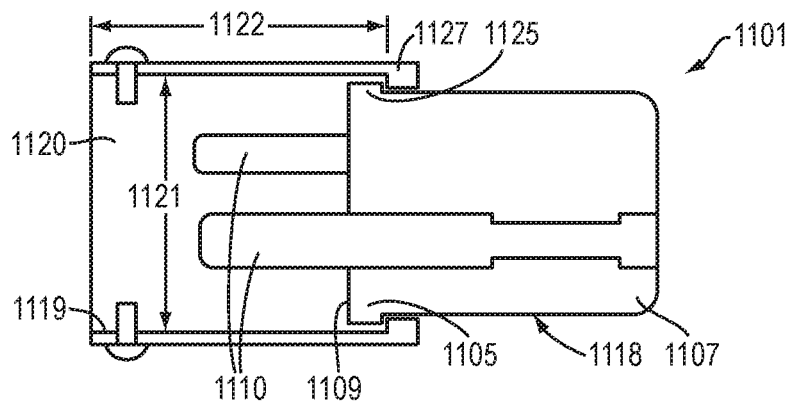

Referring now to FIGS. 11A-11C, a safety device 1101 is illustrated in accordance with one embodiment. In a various embodiments, the safety device 1101 can include an electronic apparatus, for example, the first electronic apparatus 551 illustrated in FIG. 5 for use in combination with an electronic apparatus included in the safety glasses, other eye safety hardware or other personal protective equipment, for example, the second electronic apparatus 552 also illustrated in FIG. 5. In general, the safety device 1101 operates an integral isolation device to maintain an electrical output in an off state unless the associated personal protective equipment is being worn properly.

As illustrated in FIG. 11A, the safety device 1101 includes a body 1102, a fastening device 1104 and a face 1106 in which a female electrical socket 1108 is located. In the illustrated embodiment, the body 1101 also includes a user interface 1112. The fastening device includes at least a part of a fastening system to allow the safety device 1101 to be secured to another component of an overall safety system that employs the safety device 1101 with a second component to secure the system to a power cord. According to some embodiments, the fastening device 1104 includes a hole 1129 employed in the fastening system. According to one embodiment, the fastening system includes a mechanical fastener 1116, for example, a screw. In the embodiment illustrated in FIG. 11, the hole 1129 is configured to receive a mechanical fastener 1116.

In various embodiments, the fastening device 1104 is configured to move forward and backward while attached to the body 1102 in a direction parallel to a longitudinal axis of the body 1102, for example, as indicated by the arrow A. In some embodiments, the fastening device 1104 is also free to rotate about the longitudinal axis, for example, free to rotate 360 degrees about the longitudinal axis while coupled to the body 1102.

In FIG. 11A the fastening device 1104 is illustrated in a position in which it is moved rearward in the direction of the face 1106. In FIG. 11B, a distal end 1126 and a proximate end 1128 included in the fastening device 1104 are identified. As illustrated in FIG. 11B, the fastening device 1104 is moved in a distal direction such that a majority of the fastening device extends away from the body 1102. In FIG. 11C, a distal end 1105 and a proximate end 1107 included in the body 1102 are illustrated.

In various embodiments, the user interface 1112 can include features and functionality as described with reference to the user interface 112 included in the safety device 100. For example, the user interface 1112 includes a first indicating light 1113 and a second indicating light 1114. In one embodiment, the first indicating light 1113 provides an indication of whether the safety device 1101 is connected to an energized source of electricity and the second indicating light 1114 provides a status indication concerning the state of the electrical isolation device, that is, whether the isolation device is open or closed.

A cross-sectional view of the safety device 1101 is illustrated in FIG. 11C. In accordance with the illustrated embodiment, the body 1102 includes an outer surface 1118 and a face 1109 from which a male plug 1110 extends. The fastening device 1104 includes an overall cylindrical shape including an inner wall 1119 that defines a hollow region 1120 configured to receive at least a part of the body 1102 within it. The hollow region 1120 includes a diameter 1121 and a length 1122.

In the illustrated embodiment, the fastening device includes two holes located 180 degrees opposite one another in the vicinity of the distal end 1126 of the fastening device 1104. In FIG. 11C, the holes (for example, including the hole 1129) are located a distance 1123 from the distal end 1126 of the fastening device. A fastener (for example, the fastener 1116) is located in each hole such that it extends radially inward.

Further according to the illustrated embodiment, the body 1102 includes a first abutment 1125 located at the distal end 1105 of the body. The fastening device 1104 includes a second abutment 1127 located at the proximate end 1128 of the fastening device 1104. In one embodiment, the first abutment 1125 is raised above the outer surface 1118 for 360 degrees around the body 1104. Similarly, the second abutment 1127 projects radially inward from the inner wall 1119 for a full 360 degrees around the inner wall. The preceding is advantageous where the fastening device 1104 is free to rotate about the body 1102. According to another embodiment, a longitudinal channel can be provided in the outer surface 1118 to receive a projection extending radially inward from the inner wall 1119. According to this embodiment, the fastening device 1104 does not rotate about the body 1102. As a result, the first abutment 1125 and the second abutment 1127 can be located at one or more discrete locations on the outer surface 1118 and the inner wall 1119, respectively.

In operation, the fastening device 1104 is free to move forward and back relative to the body 1102 as shown by the arrow A in FIG. 11A. For example, the fastening device 1104 can be moved in a distal direction parallel to a longitudinal axis of the body 1102 until the second abutment 1127 makes contact with the first abutment 1125.

Further, in some embodiments the body includes one or more additional abutments extending from the outer surface 1118 located at or near the proximate end 1107 of the body 1102. According to these embodiments, the additional abutment(s) limit the travel of the fastening device 1104 in a direction of the proximate end 1107 of the body 1102. That is, the fastening device 1104 is moved in the direction of the proximate end 1107 until the second abutment 1127 makes contact with the additional abutment. The preceding approach can assist in preventing the fastening device 1104 from being uncoupled from the body 1102.

Figure 12A:
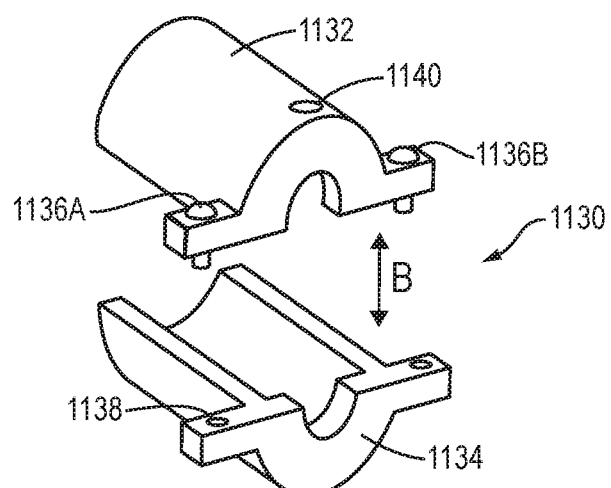
FIGS. 12A-12C illustrate a second component of the safety system in accordance with the embodiment of FIGS. 11A-11C.
Figure 12B:
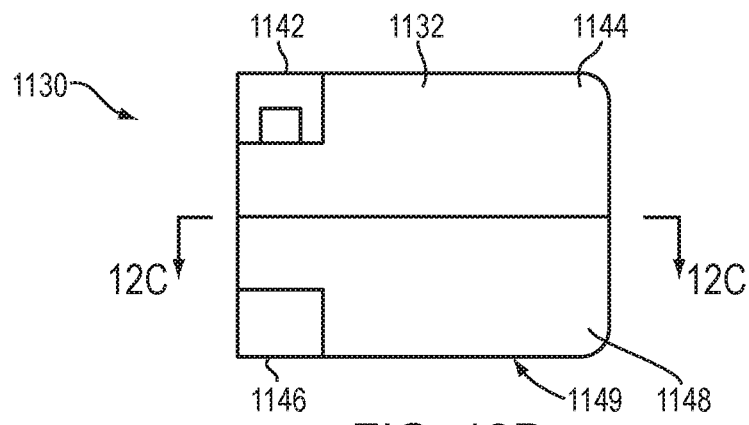
Figure 12C:
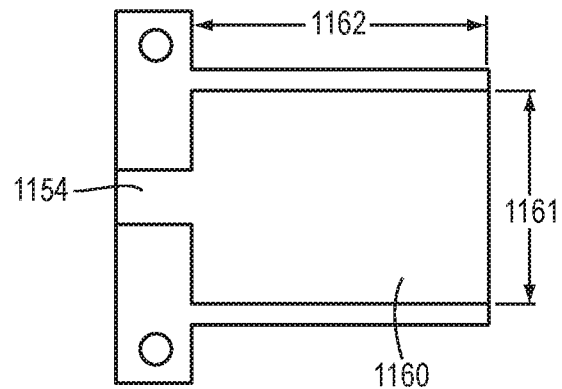

In contrast to the safety systems described with reference to FIGS. 1-6, the safety device 1101 is employed with a second component used to secure the safety device 1101 to a power cord. Referring now to FIGS. 12A-12C, a clamp 1130 is illustrated in accordance with one embodiment. As is described in greater detail below, the clamp 1130 is secured to a power cord and the safety device 1101 is fastened to the clamp with the safety device 1101 electrically coupled to the power cord. According to this embodiment, the clamp 1130 includes a first half 1132 and a second half 1134. The first half 1132 includes a first hole 1140 employed in combination with one or more elements (for example, a mechanical fastener) included in the safety device 1101 to provide a fastening system that secures the fastening device 1104 to the clamp 1130. The second half 1134 can include a second hole (not illustrated) that provides similar functionality.

According to various embodiments, the clamp 1130 includes one or more fasteners employed to secure the first half 1132 to the second half 1134. For example, a mechanical fastener 1136 is included in the illustrated embodiment. According to this embodiment, each of the first half 1132 and the second half 1134 include a hole (for example, the hole 1138) to receive the fastener 1136. In the illustrated embodiment, two holes are employed where, for example, the first half 1132 includes a smooth sided hole and the second half 1134 includes a threaded hole 1138A, 1138B.

Referring now to FIG. 12B, the clamp 1130 is illustrated in an assembled state with the first half 1132 and the second half 1134 moved together as indicated by the arrow B in FIG. 12A. As illustrated in FIG. 12B, the first half 1132 includes a proximate end 1142 and a distal end 1144. Similarly, the second half 1134 includes a proximate end 1146 and a distal end 1148. According to the illustrated embodiment, the two halves 1132, 1134 are secured together by threading multiple fasteners (for example, the mechanical fasteners 1136A, 1136B) into corresponding threaded holes (1138A, 1138B) included in the second half 1134. The clamp 1130 includes an outer surface 1149 formed with the clamp 1130 fully assembled.

In operation, the clamp 1130 is secured around a female socket located at a distal end of a power cord. When assembled, the clamp 1130 provides a cavity sized and configured to receive the female socket within it. A cross-sectional view of the assembled clamp 1130 is illustrated in FIG. 12C. In the illustrated embodiment, the clamp includes a first cavity 1154 and a second cavity 1160. The second cavity 1160 includes a diameter 1161 and a length 1162. According to this embodiment, a power cord is received in the first cavity 1154 and a female socket located at the distal end of the power cord is received in the second cavity 1160.

Figure 13A:
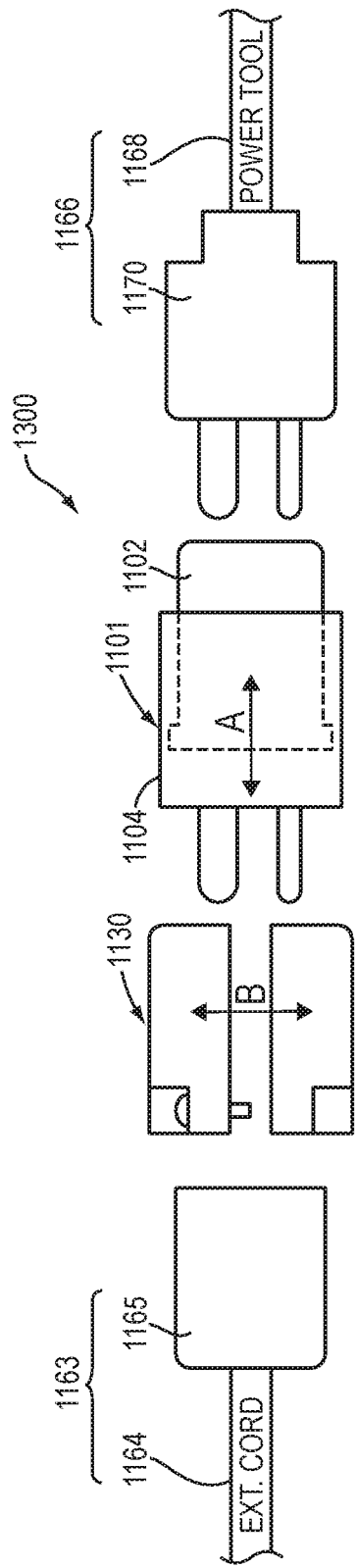
FIGS. 13A-13B illustrate the safety system including the components illustrated in FIGS. 11A-11C and 12A-12C in accordance with one embodiment.
Figure 13B:
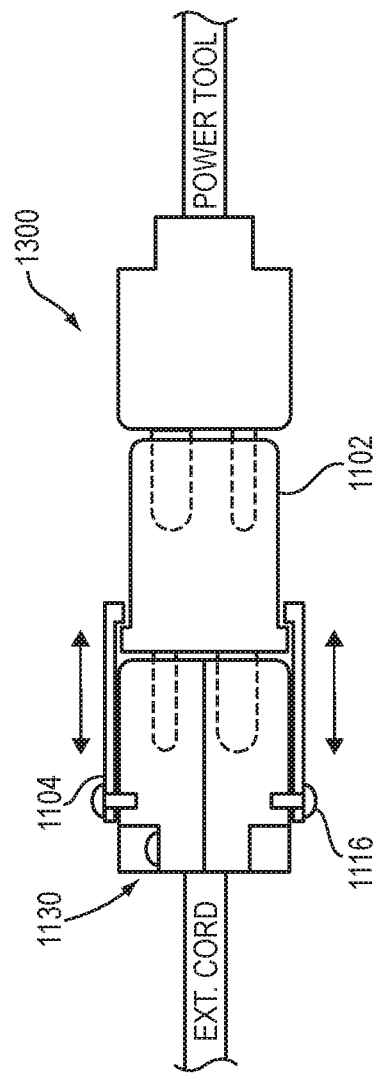

Referring now to FIGS. 13A and 13B, a safety system 1300 including the safety device 1101 and the clamp 1130 is illustrated. According to this embodiment, the safety system 1300 is employed in combination with an extension cord 1163 and an electrical cord 1166 for an electrically-operated device. The extension cord 1163 includes a power cord 1164 and a female socket 1165. The electrical cord 1166 includes a power cord 1168 and a male plug 1170. In FIG. 13A, a portion of the body 1102 located within the fastening device 1104 is shown in phantom. In FIG. 13B, the fastening device is illustrated in cross-section and the prongs of the male plugs are illustrated in phantom where they are received within a respective one of the female sockets.

FIG. 13A, illustrates the two halves 1132, 1134 being separated from one another as shown by the arrow B to allow them to be placed around the female socket 1165 and distal end of the power cord 1164. FIG. 13B illustrates the clamp 1130 secured to the extension cord 1163. In this embodiment, the female socket 1165 is sandwiched between the halves 1132, 1134 of the clamp 1130 and the face at which the female socket is plugged into remains accessible at the distal end of the second cavity 1160.

FIG. 13B illustrates the electrical cord 1166 plugged into the proximate end 1107 of the body 1102. The male plug 1110 included in the safety device 1101 is plugged into the female socket 1165 included in the extension cord 1163. In FIG. 13B, the fastening device 1104 is extended from the body 1102 is a direction of a distal end of the body. In this configuration, the clamp 1130 is received within the hollow region 1120 provided by the fastening device 1104.

FIG. 13B also illustrates an embodiment in which the safety device 1101 can be fastened to the clamp 1130. According to the illustrated embodiment, a fastening system is employed including two mechanical fasteners 1116. Each of the fasteners 1116 is inserted through a hole (for example, the hole 1129) in the fastening device 1104 and then threaded into a corresponding hole (for example, the hole 1140) included in the clamp 1130. The mechanical attachment of the safety device 1101 to the extension cord 1163 can improve safety by ensuring that the safety device 1101 cannot be detached from the extension cord 1163 without the use of tools.

Different approaches for attaching the safety device 1101 to the clamp 1130 are employed in other embodiments. For example, the mechanical fasteners 1116 can be replaced by a pushbutton release. According to a version of this embodiment, the clamp includes a spring loaded pushbutton that is biased in a radially outward direction such that a distal end of the button extends above the outer surface 1149 of the clamp 1130. The fastening device 1104 can include a hole (for example, the hole 1129) located such that the distal end of the pushbutton can be received within it when the fastening device 1104 is extended from the body to receive the clamp 1130 within the hollow region 1120. The attachment is released by depressing the distal end of the pushbutton such that the fastening device 1104 can be withdrawn from the clamp by moving the fastening device in a direction of the proximate end of the body 1102.

In yet another embodiment, the safety device 1101 is threaded onto the clamp 1130. According to this embodiment, the interior wall 1119 of the fastening device 1104 includes a set of threads. The outer surface 1149 of the clamp includes a corresponding set of threads. The body 1102 can be plugged into extension cord 1163. The fastening device 1104 is moved in a distal direction such that the threads included on the interior wall 1119 engage the threads included on the outer surface 1149. The fastening device 1104 is rotated about the longitudinal axis of the safety device 1101 to thread the safety device 1101 to the clamp 1130. To detach the safety device 1101 from the clamp 1130, the preceding process is revered.

Figure 14A:
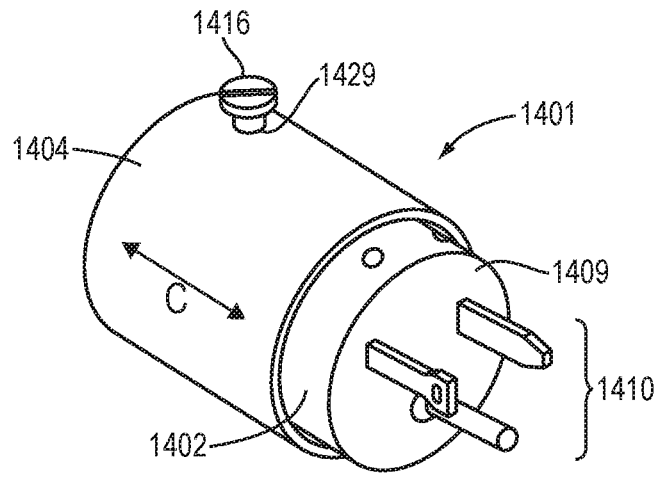
FIGS. 14A-14C illustrate a first component of a safety system in accordance with yet another embodiment.
Figure 14B:
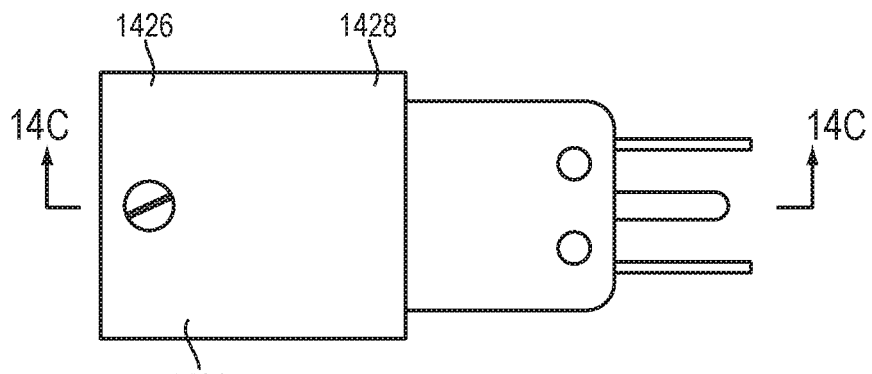
Figure 14C:
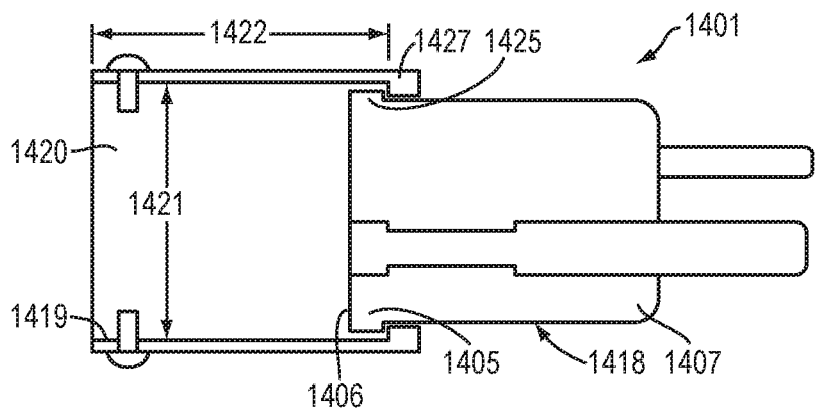

Referring now to FIGS. 14A-14C, a safety device 1401 is illustrated in accordance with another embodiment. The safety device 1401 includes a body 1402 and a fastening device 1404 coupled to the body. In general, the embodiment illustrated in FIGS. 14A-14C includes the same functionality as illustrated and described with reference to FIG. 11A-11C. However, in contrast to the safety device 1101 illustrated in FIGS. 11A-11C, the safety device 1401 is secured to a male plug rather than a female receptacle. That is, the fastening device 1404 is configured to attach to the male plug employed in a circuit that provides power to a piece of electrically operated equipment.

In a various embodiments, the safety device 1401 can include an electronic apparatus, for example, the first electronic apparatus 551 illustrated in FIG. 5 for use in combination with an electronic apparatus included in the safety glasses, other eye safety hardware or other personal protective equipment, for example, the second electronic apparatus 552 also illustrated in FIG. 5. In general, the safety device 1401 operates an integral isolation device to maintain an electrical output in an off state unless the associated personal protective equipment is being worn properly.

As illustrated in FIG. 14A, the body 1402 includes a face 1409 in which a male plug 1410 is located. In the illustrated embodiment, the body 1401 also includes a user interface 1412. The fastening device includes at least a part of a fastening system to allow the safety device 1401 to be secured to another component of an overall safety system that employs the safety device 1401 with a second component to secure the system to a power cord. According to some embodiments, the fastening device 1404 includes a hole 1429 employed in the fastening system. According to one embodiment, the fastening system includes a mechanical fastener 1416, for example, a screw. In the embodiment illustrated in FIG. 14, the hole 1429 is configured to receive a mechanical fastener 1416.

In various embodiments, the fastening device 1404 is configured to move forward and backward while attached to the body 1402 in a direction parallel to a longitudinal axis of the body 1402, for example, as indicated by the arrow C. In some embodiments, the fastening device 1404 is also free to rotate about the longitudinal axis, for example, free to rotate 360 degrees about the longitudinal axis while coupled to the body 1402.

In FIG. 14A the fastening device 1404 is illustrated in a position in which it is moved rearward in the direction of the face 1409. In FIG. 14B, a distal end 1426 and a proximate end 1428 included in the fastening device 1404 are identified. In FIG. 14B, the fastening device 1404 is moved in a distal direction such that a majority of the fastening device extends away from the body 1402. In FIG. 14C, a distal end 1405 and a proximate end 1407 included in the body 1402 are illustrated. According to the illustrated embodiment, a user interface 1412 is located at the proximate end 1407 of the body 1402. The user interface 1412 can include features and functionality as described with reference to the user interface 112 included in the safety device 100.

A cross-sectional view of the safety device 1401 is illustrated in FIG. 14C. In accordance with the illustrated embodiment, the body 1402 includes an outer surface 1418 and a face 1409 from which a male plug 1410 extends. The fastening device 1404 includes an overall cylindrical shape including an inner wall 1419 that defines a hollow region 1420 configured to receive at least a part of the body 1402 within it. The hollow region 1420 includes a diameter 1421 and a length 1422.

In the illustrated embodiment, the fastening device includes two holes located 180 degrees opposite one another in the vicinity of the distal end 1426 of the fastening device 1404. In FIG. 14C, the holes (for example, including the hole 1429) are located a distance 1423 from the distal end 1426 of the fastening device. A fastener (for example, the fastener 1416) is located in each hole such that it extends radially inward.

Further according to the illustrated embodiment, the body 1402 includes a first abutment 1425 located at the distal end 1405 of the body. The fastening device 1404 includes a second abutment 1427 located at the proximate end 1428 of the fastening device 1404. In one embodiment, the first abutment 1425 is raised above the outer surface 1418 for 360 degrees around the body 1404. Similarly, the second abutment 1427 projects radially inward from the inner wall 1419 for a full 360 degrees around the inner wall. The preceding is advantageous where the fastening device 1404 is free to rotate about the body 1402. According to another embodiment, a longitudinal channel can be provided in the outer surface 1418 to receive a projection extending radially inward from the inner wall 1419. According to this embodiment, the fastening device 1404 does not rotate about the body 1402. As a result, the first abutment 1425 and the second abutment 1427 can be located at one or more discrete locations on the outer surface 1418 and the inner wall 1419, respectively.

In operation, the fastening device 1404 is free to move forward and back relative to the body 1402 as shown by the arrow A in FIG. 14A. For example, the fastening device 1404 can be moved in a distal direction parallel to a longitudinal axis of the body 1402 until the second abutment 1427 makes contact with the first abutment 1425.

Further, in some embodiments the body includes one or more additional abutments extending from the outer surface 1418 located at or near the proximate end 1407 of the body 1402. According to these embodiments, the additional abutment(s) limit the travel of the fastening device 1404 in a direction of the proximate end 1407 of the body 1402. That is, the fastening device 1404 is moved in the direction of the proximate end 1407 until the second abutment 1427 makes contact with the additional abutment. The preceding approach can assist in preventing the fastening device 1404 from being uncoupled from the body 1402.

Figure 15A:
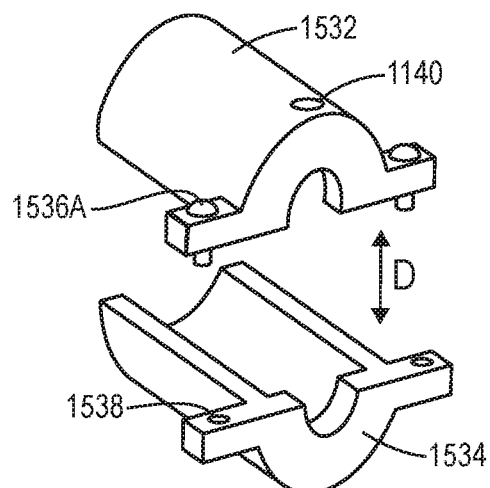
FIGS. 15A-15C illustrate a second component of the safety system in accordance with the embodiment of FIGS. 14A-14C.
Figure 15B:
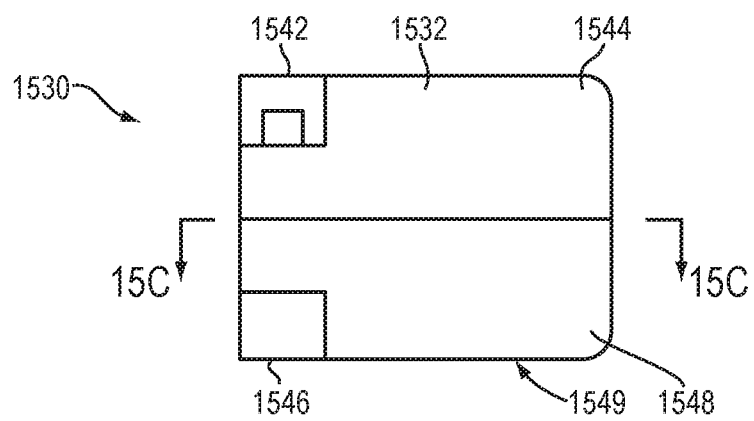
Figure 15C:
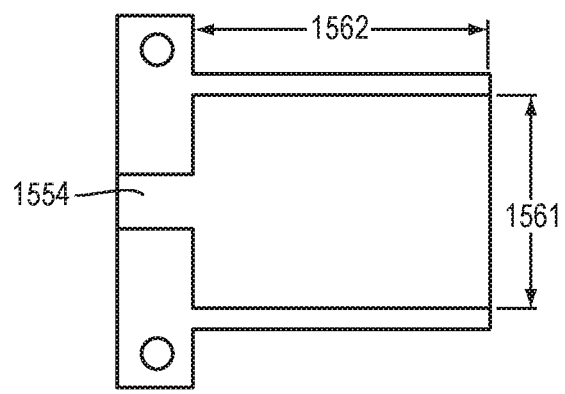

Referring now to FIGS. 15A-15C, a clamp 1530 is illustrated in accordance with one embodiment. As is described in greater detail below, the clamp 1530 is secured to a power cord and the safety device 1401 is fastened to the clamp with the safety device 1401 electrically coupled to the power cord. According to this embodiment, the clamp 1530 includes a first half 1532 and a second half 1534. The first half 1532 includes a first hole 1540 employed in combination with one or more elements (for example, a mechanical fastener) included in the safety device 1401 to provide a fastening system that secures the fastening device 1404 to the clamp 1530. The second half 1534 can include a second hole (not illustrated) that provides similar functionality.

According to various embodiments, the clamp 1530 includes one or more fasteners employed to secure the first half 1532 to the second half 1534. For example, a mechanical fastener 1536 is included in the illustrated embodiment. According to this embodiment, each of the first half 1532 and the second half 1534 include a hole (for example, the hole 1538) to receive the fastener 1536. In the illustrated embodiment, two holes and two fasteners are employed where, for example, the first half 1532 includes a smooth sided hole and the second half 1534 includes a threaded hole 1538A, 1538B.

Referring now to FIG. 15B, the clamp 1530 is illustrated in an assembled state with the first half 1532 and the second half 1534 moved together as indicated by the arrow D in FIG. 15A. As illustrated in FIG. 15B, the first half 1532 includes a proximate end 1542 and a distal end 1544. Similarly, the second half 1534 includes a proximate end 1546 and a distal end 1548. According to the illustrated embodiment, the two halves 1532, 1534 are secured together by threading multiple fasteners (for example, the mechanical fasteners 1536A, 1536B) into corresponding threaded holes (1538A, 1538B) included in the second half 1534. The clamp 1530 includes an outer surface 1549 formed with the clamp 1530 fully assembled.

In operation, the clamp 1530 is secured around a female socket located at a distal end of a power cord. When assembled, the clamp 1530 provides a cavity sized and configured to receive the female socket within it. A cross-sectional view of the assembled clamp 1530 is illustrated in FIG. 15C. In the illustrated embodiment, the clamp includes a first cavity 1554 and a second cavity 1560. The second cavity 1560 includes a diameter 1561 and a length 1562. According to this embodiment, a power cord is received in the first cavity 1554 and a female socket located at the distal end of the power cord is received in the second cavity 1560.

Figure 16A:
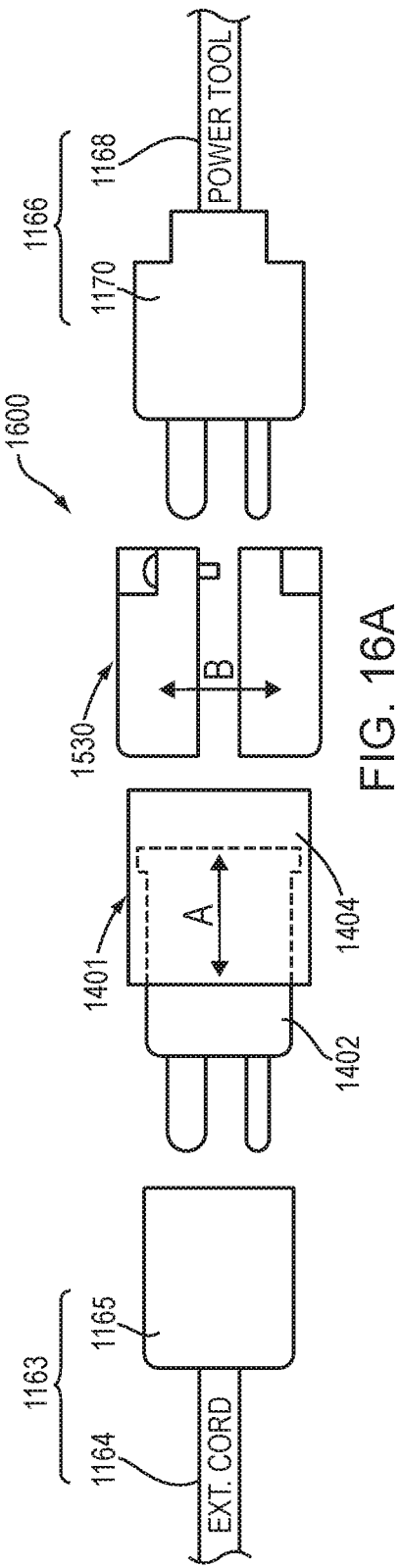
FIGS. 16A-16B illustrate the safety system including the components illustrated in FIGS. 14A-14C and 15A-15C in accordance with one embodiment.
Figure 16B:
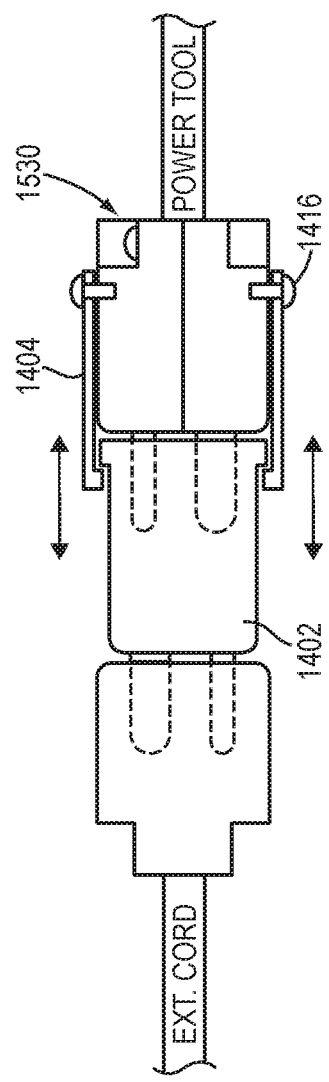

Referring now to FIGS. 16A and 16B, a safety system 1600 including the safety device 1401 and the clamp 1530 is illustrated. According to this embodiment, the safety system 1600 is employed in combination with the extension cord 1163 and the electrical cord 1166 for an electrically-operated device. The extension cord 1163 includes the power cord 1164 and the female socket 1165. The electrical cord 1166 includes the power cord 1168 and the male plug

1170. In FIG. 16A, a portion of the body 1402 located within the fastening device 1404 is shown in phantom. In FIG. 16B, the fastening device is illustrated in cross-section and the prongs of the male plugs are illustrated in phantom where they are received within the respective female sockets.

FIG. 16A, illustrates the two halves 1532, 1534 being separated from one another as shown by the arrow B to allow them to be placed around the male plug 1170 and distal end of the power cord 1168. FIG. 16B illustrates the clamp 1530 secured to the electrical cord 1166. In this embodiment, the male plug 1170 is sandwiched between the halves 1532, 1534 of the clamp 1530 and the face at which the male plug is located remains accessible at the distal end of the second cavity 1560.

FIG. 16B illustrates the electrical cord 1166 plugged into the distal end 1405 of the body 1402. The male plug 1410 included in the safety device 1401 is plugged into the female socket 1165 included in the extension cord 1163. In FIG. 16B, the fastening device 1404 is extended from the body 1402 is a direction of a distal end of the body. In this configuration, the clamp 1530 is received within the hollow region 1420 provided by the fastening device 1404.

FIG. 16B also illustrates an embodiment in which the safety device 1401 can be fastened to the clamp 1530. According to the illustrated embodiment, a fastening system is employed including two mechanical fasteners 1416. Each of the fasteners 1416 is inserted through a hole (for example, the hole 1429) in the fastening device 1404 and then threaded into a corresponding hole (for example, the hole 1540) included in the clamp 1530. The mechanical attachment of the safety device 1401 to the power cord 1166 can improve safety by ensuring that the safety device 1401 cannot be detached from the power cord 1166 without the use of tools.

While the safety systems illustrated and described herein are employed with personal safety equipment in the form of safety glasses, according to other embodiments, systems can employ the safety systems illustrated and described (safety systems 100, 400, 600, 700, 800, 900, 1100, 1200, 1300, 1600) with other forms of personal protective equipment including goggles (and other types of eye protection equipment), hardhats, gloves, respirators and articles of clothing (for example, lab coats and flame retardant garments).

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

What is claimed is:

1. An apparatus for use with an item of personal protective equipment, the item of personal protective equipment including a first wireless communication device and a sensor configured to detect when the personal protective equipment is being worn properly by a user, the apparatus configured to be housed within a hand-held battery-operated power tool that includes a power circuit to supply electrical power for operation of the hand-held battery-operated power tool and a removable battery pack, the apparatus comprising:
    an electrical isolation device configured to be housed within the removable battery pack to prevent current flow in at least one conductor included in the power circuit; and
    a second wireless communication device configured to wirelessly couple to the first wireless communication device,
    wherein the second wireless communication device is configured to receive a wireless signal transmitted from the first wireless communication device, the wireless signal providing information concerning whether the user is wearing the item of personal protective equipment properly,
    wherein the electrical isolation device operates to allow current flow in the at least one conductor when the information provided by the wireless signal indicates that the item of personal protective equipment is being worn properly by the user, and
    wherein the apparatus is configured to place the electrical isolation device in a state that allows a flow of charging current when the removable battery pack is removed from the hand-held power tool for charging regardless of whether the item of personal protective equipment is being worn properly by the user.

2. The apparatus of claim 1, further comprising a user interface configured to provide an indication of an operating state of the electrical isolation device,
    wherein the apparatus is oriented within the hand-held battery-operated power tool to allow the user interface to be viewed by a user operating the hand-held battery-operated power tool.

3. The apparatus of claim 2, further comprising a processor coupled to each of the electrical isolation device, the second wireless communication device and the user interface,
    wherein the processor is configured to process information provided by the second wireless communication device to determine whether the item of personal protective equipment is being worn properly by the user, and
    wherein the processor is configured to provide a signal to control the state of the electrical isolation device based on the determination.

4. The apparatus of claim 1, wherein the apparatus is configured to automatically place the electrical isolation device in the state that allows the flow of charging current when the removable battery pack is removed from the hand-held battery-operated power tool.

5. The apparatus of claim 1, further comprising a user interface configured to provide an indication of an operating state of the electrical isolation device,
    wherein the apparatus is oriented within the hand-held battery-operated power tool to allow the user interface to be viewed by a user operating the hand-held battery-operated power tool.

6. The apparatus of claim 5, further comprising a processor coupled to each of the electrical isolation device, the second wireless communication device and the user interface,
    wherein the processor is configured to process information provided by the second wireless communication device to determine whether the item of personal protective equipment is being worn properly by the user, and
    wherein the processor is configured to provide a signal to control the state of the electrical isolation device based on the determination.

7. The apparatus of claim 5, wherein the removable battery pack is provided as a retrofit for a battery pack originally supplied with the hand-held battery-operated power tool.

8. The apparatus of claim 1, further comprising a user interface including at least one indicating light configured to indicate: a) when the second wireless communication device is in wireless communication with the first wireless communication device; and b) whether the information included in the wireless signal indicates that the user is wearing the item of personal protective equipment properly.

9. A hand held battery-operated power tool including the apparatus of claim 1.

10. A battery pack including the apparatus of claim 1.

11. An apparatus for use with a pair of safety glasses, the safety glasses including a first wireless communication device and a sensor configured to detect when the personal protective equipment is being worn properly by a user, the apparatus configured to be housed within a hand-held battery-operated power tool that includes a power circuit to supply electrical power for operation of the hand-held battery-operated power tool, the apparatus comprising:

an electrical isolation device configured to prevent current flow in at least one conductor included in the power circuit;

a second wireless communication device configured to wirelessly couple to the first wireless communication device to receive a wireless signal that indicates whether the pair of safety glasses is being worn properly by the user; and a user interface including at least one indicating light configured to indicate when the second wireless communication device is in wireless communication with the first wireless communication device included in the safety glasses, wherein the electrical isolation device operates to allow current flow in the at least one conductor when the information included in the wireless signal indicates that the pair of safety glasses is being worn properly by the user;

wherein the apparatus is included in a removable battery pack, and wherein the apparatus is configured to place the electrical isolation device in a state that allows a flow of charging current when the removable battery pack is removed from the hand-held battery-operated power tool for charging regardless of whether the safety glasses are being worn properly by the user.

12. The apparatus of claim 11, wherein the at least one indicating light is configured to indicate an operating state of the electrical isolation device.

13. The apparatus of claim 12, wherein the at least one indicating light includes a plurality of indicating lights including a first indicating light to indicate when the second wireless communication device is in wireless communication with the first wireless communication device included in the safety glasses and a second indicating light to indicate the operating state of the electrical isolation device.

14. The apparatus of claim 13, wherein the user interface is included in the battery pack.

15. The apparatus of claim 14, wherein the user interface is oriented within the hand-held battery-operated power tool to allow the user interface to be viewed by a user operating the hand-held battery-operated power tool.

\* \* \* \* \*